(12) United States Patent
Paul et al.

(10) Patent No.: US 10,718,728 B2
(45) Date of Patent: Jul. 21, 2020

(54) IN-VITRO SENSOR USING A TETRAPOLAR IMPEDANCE MEASUREMENT

(71) Applicant: Trividia Health, Inc., Fort Lauderdale, FL (US)

(72) Inventors: Patrick J. Paul, Boca Raton, FL (US); Brent E. Modzelewski, Boca Raton, FL (US)

(73) Assignee: Trividia Health, Inc., Fort Lauderdale, FL (US)

( * ) Notice: Subject to any disclaimer, the term of this patent is extended or adjusted under 35 U.S.C. 154(b) by 205 days.

(21) Appl. No.: 15/381,720

(22) Filed: Dec. 16, 2016

(65) Prior Publication Data

US 2017/0176366 A1 Jun. 22, 2017

Related U.S. Application Data

(63) Continuation of application No. PCT/US2016/067028, filed on Dec. 15, 2016.
(Continued)

(51) Int. Cl.
*G01N 27/327* (2006.01)
*G01N 27/02* (2006.01)
(Continued)

(52) U.S. Cl.
CPC ....... *G01N 27/026* (2013.01); *A61B 5/14532* (2013.01); *G01N 27/028* (2013.01);
(Continued)

(58) Field of Classification Search
CPC .......... G01N 27/3272; G01N 27/3273; G01N 27/3274
See application file for complete search history.

(56) References Cited

U.S. PATENT DOCUMENTS 4,204,545 A * 5/1980 Yamakoshi ............ A61B 5/022
600/493
4,547,735 A * 10/1985 Kiesewetter ........... G01N 33/49
324/442
(Continued)

FOREIGN PATENT DOCUMENTS

WO 2004/049937 A1 6/2004
WO 2005/074796 A1 8/2005
(Continued)

OTHER PUBLICATIONS

U.S. Appl. No. 60/480,243, filed Jun. 20, 2003 (Year: 2003).*
(Continued)

*Primary Examiner* — Alexander S Noguerola
(74) *Attorney, Agent, or Firm* — Greenberg Traurig LLP; David J. Dykeman; Roman Fayerberg

(57) ABSTRACT

Systems, methods, and devices are provided for determining an impedance measurement of a sample of fluid on a test strip having a base layer, at least two drive electrodes disposed on the base layer and in electrical communication with a current-source ($I_{ac}$) for flowing an AC current provided by the current-source ($I_{ac}$) through a fluid sample between the at least two drive electrodes, and at least two sense electrodes disposed on the base layer and positioned between the at least two drive electrodes, each of the at least two sense electrodes configured for measuring a difference in an AC potential therebetween to determine an impedance measurement of the fluid sample between the at least two sense electrodes.

27 Claims, 19 Drawing Sheets

Related U.S. Application Data

(60) Provisional application No. 62/269,277, filed on Dec. 18, 2015.

(51) Int. Cl.
  *G01N 33/49* (2006.01)
  *A61B 5/145* (2006.01)

(52) U.S. Cl.
  CPC ..... *G01N 27/3273* (2013.01); *G01N 27/3274* (2013.01); *G01N 33/49* (2013.01); *A61B 5/14535* (2013.01); *A61B 2562/0295* (2013.01); *G01N 27/3272* (2013.01)

(56) References Cited

U.S. PATENT DOCUMENTS

| | | | | |
|---|---|---|---|---|
| 5,526,808 | A * | 6/1996 | Kaminsky | A61B 5/053 600/370 |
| 6,058,934 | A * | 5/2000 | Sullivan | G01N 33/4915 204/409 |
| 7,867,369 | B2 * | 1/2011 | Bhullar | G01N 27/3272 204/403.01 |
| 2004/0128088 | A1 * | 7/2004 | Laletin | G01N 27/4161 702/64 |
| 2007/0015286 | A1 * | 1/2007 | Neel | G01N 33/48771 436/149 |
| 2010/0234701 | A1 | 9/2010 | Cho et al. | |
| 2015/0068926 | A1 | 3/2015 | Ringer et al. | |
| 2015/0083613 | A1 * | 3/2015 | Lee | G01N 33/66 205/782 |
| 2015/0176049 | A1 | 6/2015 | Elder et al. | |

FOREIGN PATENT DOCUMENTS

| | | |
|---|---|---|
| WO | 2008/030757 A1 | 3/2008 |
| WO | 2014198428 A1 | 12/2014 |

OTHER PUBLICATIONS p. 1 of Chapter 1 and Chapter 4 of BME/EECS 458—Biomedical Instrumentation & Design, Matt O'Donnell, published 2002 (Year: 2002).*

International Search Report in International Patent Application No. PCT/US2016/067028 dated Mar. 9, 2017.

* cited by examiner

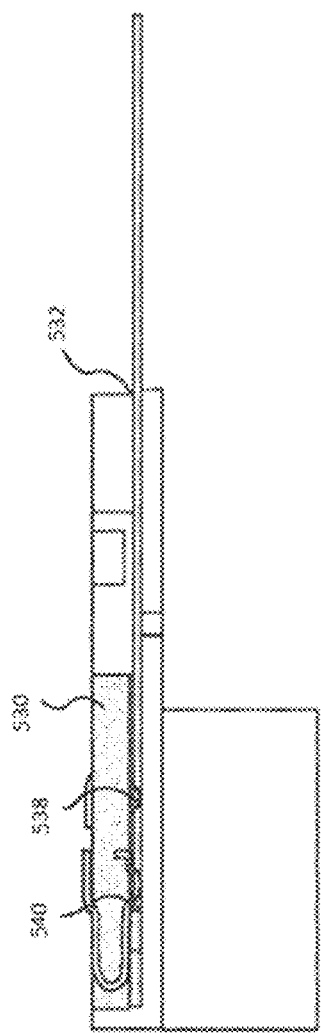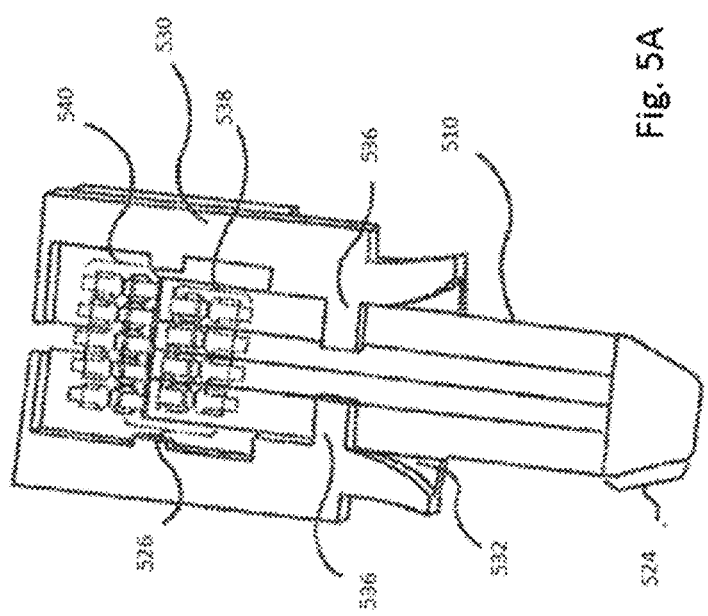
Fig. 5B
Fig. 5A

IN-VITRO SENSOR USING A TETRAPOLAR IMPEDANCE MEASUREMENT

CROSS-REFERENCE TO RELATED APPLICATIONS

This application claims priority to and the benefit of U.S. Provisional Application No. 62/269,277, filed Dec. 18, 2015 and PCT International Patent Application No. PCT/US2016/067028, filed Dec. 15, 2016, the contents of each of which are incorporated herein in their entireties.

FIELD

The present disclosure relates to systems and methods for electrochemically sensing a particular constituent within a fluid through the use of diagnostic test strips and, more particularly, to in-vitro impedance testing such as in-vitro glucose testing.

BACKGROUND

Many industries have a commercial need to monitor the concentration of particular constituents in a fluid. In the health care field, individuals with diabetes, for example, have a need to monitor a particular constituent within their bodily fluids. A number of systems are available that allow people to test a body fluid, such as, blood, urine, or saliva, to conveniently monitor the level of a particular fluid constituent, such as, for example, cholesterol, proteins, and glucose. Such systems typically include a test strip where the user applies a fluid sample and a meter that "reads" the test strip to determine the level of the tested constituent in the fluid sample.

It would be advantageous to have a system which would allow for more accurate measurement of an analyte concentration in a body fluid.

SUMMARY

In accordance with various embodiments, a test strip is provided. The test strip includes a base layer. The test strip also includes at least two drive electrodes disposed on the base layer and in electrical communication with a current-source ($I_{ac}$) for flowing an AC current provided by the current-source ($I_{ac}$) through a fluid sample between the at least two drive electrodes. The test strip also includes at least two sense electrodes disposed on the base layer and positioned between the at least two drive electrodes, each of the at least two sense electrodes configured for measuring a difference in an AC potential therebetween to determine an impedance measurement of the fluid sample between the at least two sense electrodes.

In some embodiments, the current-source ($I_{ac}$) is programmable in amplitude and frequency. In some embodiments, the current-source ($I_{ac}$) is produced from a power source. In some embodiments, the AC current flows through the fluid sample alternatively from a first one of the at least two drive electrodes to another one of the at least two drive electrodes as determined by a frequency of the AC current provided by the current-source ($I_{ac}$). In some embodiments, the at least two sense electrodes are in electrical communication with a high input-impedance voltage measurement circuit to measure the difference in AC potential between the at least two sense electrodes. In some embodiments, the high input-impedance voltage measurement circuit includes a voltmeter configured to reduce the AC current flowing between the at least two sense electrodes and the voltmeter such that the at least two sense electrodes are not subject to an electrode polarization impedance resulting from charge transfer between the at least two sense electrodes. In some embodiments, the at least two sense electrodes of the test strip being in electrical communication with the voltmeter, the voltmeter capable of measuring the difference in the AC potential between the at least two sense electrodes to determine the impedance measurement, such that the impedance measurement is not subject to an electrode polarization impedance of the at least two drive electrodes.

In accordance with various embodiments a diagnostic meter is provided. The diagnostic meter includes a channel having a proximal end and a distal end for receiving a test strip. The diagnostic meter also includes at least two drive electrode contacts positioned in the channel to contact at least two drive electrodes of the test strip received in the channel. The diagnostic meter also includes a current-source ($I_{ac}$) for providing an AC current to the at least two drive electrodes of the test strip via the at least two drive electrode contacts. The diagnostic meter also includes at least two sense electrode contacts positioned in the channel to contact at least two sense electrodes of the test strip received in the channel. The diagnostic meter also includes a high input-impedance voltage measurement circuit to measure a difference in AC potential between the at least two sense electrodes.

In some embodiments, the proximal end of the channel is flared out to receive the test strip. In some embodiments, the connector further comprises tangs extending a predetermined height above a base of the channel and wherein the test strip is received between the base of the channel and the tangs. In some embodiments, the diagnostic meter also includes an instrumentation amplifier in electrical communication with the at least two sense electrode contacts for amplifying the measured difference in AC potential between the at least two sense electrodes. In some embodiments, the diagnostic meter also includes one or more calibration circuits for selective connection between the current-source ($I_{ac}$) and the instrumentation amplifier. In some embodiments, the diagnostic meter also includes one or more of a rectifier, an integrator, an analog to digital converter, a phase-angle detection circuit, or combinations thereof in electrical communication with the instrumentation amplifier.

In accordance with various embodiments, a system for measuring glucose concentration is provided. The system includes a test strip comprising a base layer, at least two drive electrodes disposed on the base layer and in electrical communication with a current-source ($I_{ac}$) for flowing an AC current provided by the current-source ($I_{ac}$) through a fluid sample between the at least two drive electrodes, and at least two sense electrodes disposed on the base layer and positioned between the at least two drive electrodes, the each of the at least two sense electrodes configured for measuring a difference in an AC potential therebetween to determine an impedance measurement of the fluid sample between the at least two sense electrodes. The system also includes a diagnostic meter comprising a channel having a proximal end and a distal end for receiving the test strip, at least two drive electrode contacts positioned in the channel to contact the at least two drive electrodes of the test strip received in the channel, the current-source ($I_{ac}$) for providing the AC current to the at least two drive electrodes of the test strip via the at least two drive electrode contacts, at least two sense electrode contacts positioned in the channel to contact the at least two sense electrodes of the test strip received in the channel, and a high input-impedance voltage measurement circuit to measure the difference in AC potential between the at least two sense electrodes.

In some embodiments, the current-source ($I_{ac}$) is programmable in amplitude and frequency. In some embodiments, the current-source ($I_{ac}$) is produced from a power source. In some embodiments, the AC current flows through the fluid sample alternatively from a first one of the at least two drive electrodes to another one of the at least two drive electrodes as determined by a frequency of the AC current provided by the current-source ($I_{ac}$). In some embodiments, the high input-impedance voltage measurement circuit includes a voltmeter configured to reduce the AC current flowing between the at least two sense electrodes and the voltmeter such that the at least two sense electrodes are not subject to an electrode polarization impedance resulting from charge transfer between the at least two sense electrodes. In some embodiments, the at least two sense electrodes of the test strip being in electrical communication with the voltmeter, the voltmeter capable of measuring the difference in the AC potential between the at least two sense electrodes to determine the impedance measurement, such that the impedance measurement is not subject to an electrode polarization impedance of the at least two drive electrodes. In some embodiments, the system also includes an instrumentation amplifier in electrical communication with the at least two sense electrode contacts for amplifying the measured difference in AC potential between the at least two sense electrodes. In some embodiments, the system also includes one or more calibration circuits for selective connection between the current-source ($I_{ac}$) and the instrumentation amplifier. In some embodiments, the system also includes one or more of a rectifier, an integrator, an analog to digital converter, a phase-angle detection circuit, or combinations thereof in electrical communication with the instrumentation amplifier.

In accordance with various embodiments, a method for making a test strip is provided. The method includes providing a base layer. The method also includes forming a capillary chamber on the base layer. The method also includes forming at least two drive electrodes on the base layer. The method also includes forming at least two sense electrodes on the base layer and positioned between the at least two drive electrodes such that an AC current flowing through a fluid sample received in the capillary chamber between the at least two drive electrodes flows across each of the at least two sense electrodes.

In some embodiments, the method also includes forming a fill-detect electrode on the base layer at an end of the capillary chamber for contacting the fluid sample when the capillary chamber is substantially full.

In accordance with various embodiments, a method for measuring glucose concentration is provided. The method includes receiving a fluid sample in a test strip. The method also includes flowing, through the fluid sample between at least two drive electrodes of the test strip, an AC current. The method also includes measuring, by at least two sense electrodes positioned between the at least two drive electrodes, a difference in an AC potential between the at least two sense electrodes to determine an impedance measurement of the fluid sample between the at least two sense electrodes.

In some embodiments, the method also includes amplifying, by an instrumentation amplifier in electrical communication with the at least two sense electrodes, the measured difference in AC potential between the at least two sense electrodes. In some embodiments, the method also includes providing, by a current-source ($I_{ac}$), the AC current to the first and second drive electrodes. In some embodiments, the method also includes reducing, by a high input-impedance voltage measurement circuit, the AC current flowing between the at least two sense electrodes and the high input-impedance voltage measurement circuit such that the at least two sense electrodes are not subject to an electrode polarization impedance resulting from charge transfer between the at least two sense electrodes.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 5A shows a top view of a test strip inserted into a meter, according to some embodiments of the present disclosure;

FIG. 5B is a side view of a test strip inserted into a meter, according to some embodiments of the present disclosure.

Figure 1A:
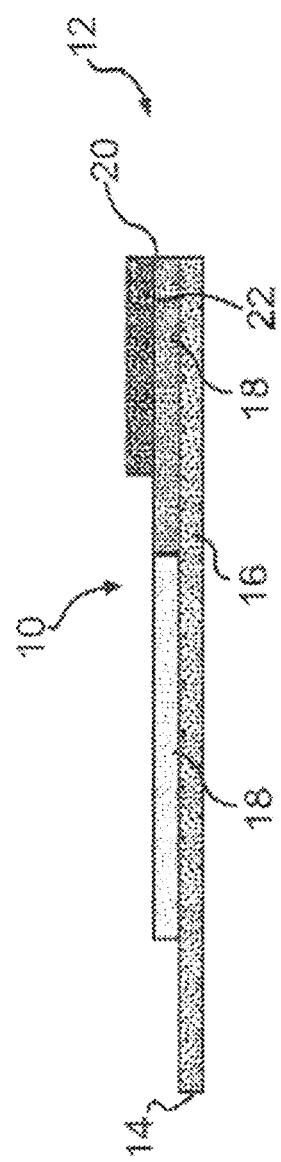
FIG. 1A is a side view of a test strip according to some embodiments of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the invention may be shown as components in block diagram form in order not to obscure the embodiments in unnecessary detail. In other instances, well-known processes, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

In accordance with the present disclosure, provided herein are electrochemical sensors developed for measuring a concentration of an analyte, such as glucose, in a fluid sample, such as blood. It should be noted that while the systems and methods of the present disclosure will be described in connection with measuring a concentration of glucose in blood, the systems and methods of the present disclosure can be used to measure other analytes in a variety of fluids.

According to aspects of the present disclosure, it is possible to use an enhanced electrode configuration for a disposable test strip for a more accurate measurement of the analytes. The disposable test strips of the present disclosure may mitigate, among other things: (1) the electrode polarization errors; and (2) the errors resulting from the actual resistance of the electrode traces on the disposable strip. Furthermore, aspects of the present disclosure can provide for a strip layout technique(s) that can reduce errors due to parasitic stray capacitance(s) between electrodes and their traces.

According to aspects of the present disclosure, stimulation electrodes and measurement electrodes may be separated. For example, a constant current can be injected via one pair of electrodes (current-injecting or "drive" electrodes) and the resulting impedance-dependent voltage can be measured with a second pair of electrodes (voltage-sensing electrodes) that are physically located between the drive electrodes, in order to be in the path of the injected current. Further, with the voltage measuring circuit having a high input impedance, the systems of the present disclosure can be insensitive to changes in the electrode or sample impedances of the voltage-sensing electrodes. Furthermore, as a constant current source is used, the system of the present disclosure can be insensitive to changes in the electrode/sample impedances of the drive electrodes. In some embodiments, this may result in the reduction of electrodes artifacts and a resulting improvement in accuracy, among other things.

FIG. 1A illustrates a general cross-sectional view of an embodiment of a test strip 10 consistent with the present invention. In some embodiments, the test strip of the present disclosure can be formed using materials and methods described in commonly owned U.S. Pat. No. 6,743,635 and U.S. patent application Ser. No. 11/181,778, which are hereby incorporated by reference in their entireties. In some embodiments, the test strip 10 may include a proximal connecting end 12, a distal end 14, and is formed with a base layer 16 extending along the entire length of test strip 10. For purposes of this disclosure, "distal" refers to the portion of a test strip further from the fluid source (i.e., closer to the meter) during normal use, and "proximal" refers to the portion closer to the fluid source (e.g., a fingertip with a drop of blood for a glucose test strip) during normal use. Base layer 16 may be composed of an electrically insulating material and has a thickness sufficient to provide structural support to test strip 10. In some embodiments, the base layer 16 includes an electrically conductive layer covered with an electrically insulating material.

Figure 1B:
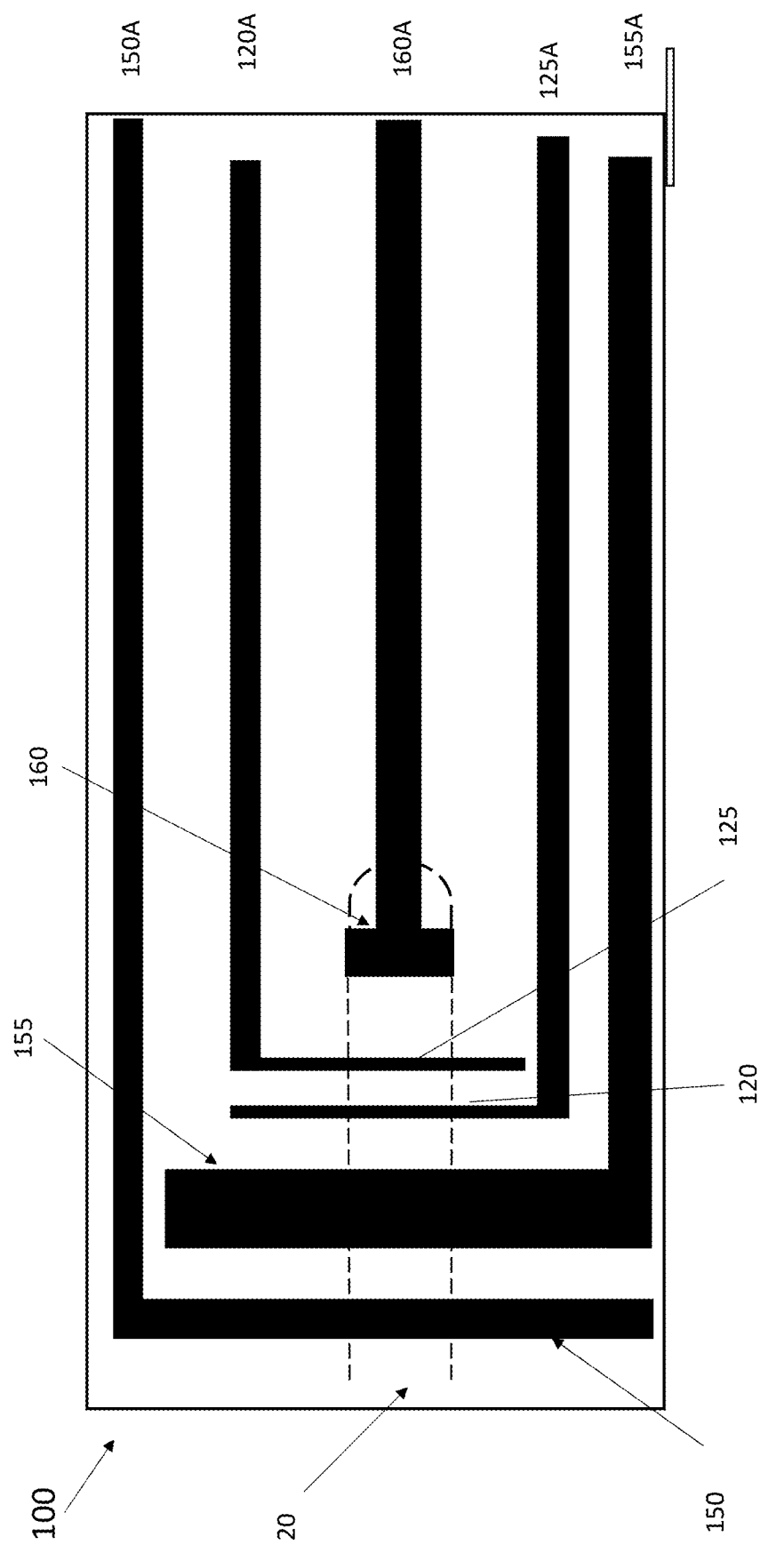
FIG. 1B illustrates a top plan view of an integrated disposable test strip, according to some embodiments of the present disclosure.

Referring to FIG. 1B, in some embodiments, a conductive pattern may be formed by laser ablating the electrically insulating material of the base layer 16 to expose the electrically conductive material underneath. Other methods may also be used to dispose the conductive pattern on the base layer. The conductive pattern includes a plurality of electrodes 120, 125, 150, 155, 160 disposed on base layer 16 near proximal end 12, and a plurality of conductive traces electrically connecting the electrodes to a plurality of electrical strip contacts (not shown) to enable the meter to read current between the electrodes. In some embodiments, the plurality of electrodes may include a working electrode, a counter electrode, and fill-detect electrodes. In some embodiments, the conductive pattern may include multiple working electrodes for measuring different analytes, constituents or characteristics of the body fluid being tested. A constituent can be any defined component of the blood such as glucose, red blood cells, plasma, proteins, salts, etc. An analyte can be a compound that is the object of a chemical (electrochemical, immunochemical) analysis or measurement. Common analytes are glucose, cholesterol, hormones, etc. A characteristic can be a property or quality of the blood that is reflective of its constituents in the aggregate. Some blood characteristics of interest are temperature, conductivity (resistivity), hematocrit, viscosity, etc. In some embodiments, the test strips of the present disclosure are configured to measure glucose concentration in a blood sample. The electrode system for measuring glucose of the test strip may include a working electrode and a reference electrode, which may be covered with a reagent layer comprising a mediator and an enzyme. A reagent layer can be disposed in a capillary chamber 20 and optionally contact at least one electrode. The reagent layer may include an enzyme, such as glucose oxidase, and a mediator, such as potassium ferricyanide or ruthenium hexamine.

Referring to FIG. 1A and FIG. 1B, a dielectric insulating layer 18 may be formed over the conductive pattern along a portion of the test strip 10 between the measuring electrodes (not shown) and the plurality of electrical strip contacts (not shown) in order to prevent scratching, and other damage, to the electrical connection. As seen in FIG. 1A, the proximal end 12 of test strip 10 (i.e. disposable test strip) may include a sample receiving location, such as the capillary chamber 20 configured to receive a user's fluid sample. The capillary chamber 20 may be formed in part through a slot formed between a cover 22 and the underlying measuring electrodes formed on base layer 16. The capillary chamber 20 has a first opening in the proximal end 12 of the test strip 10 and a second opening for venting the capillary chamber 20. The capillary chamber 20 may be dimensioned so as to be able to draw the blood sample in through the first opening, and to hold the blood sample in the capillary chamber 20, by capillary action. The test strip 10 may include a tapered section (not shown) that is narrowest at the proximal end, in order to make it easier for the user to locate the first opening and apply the blood sample.

In some embodiments, the test strips of the present disclosure also measure impedance in the test strip electrical circuit which may impact the accuracy of the analyte concentration measurement. In some instances, the measurements of analyte concentration may be adversely effected by the presence of certain blood components that may undesirably influence the measurement and lead to inaccuracies in the detection signal. This condition may result in inaccurate reported blood analyte reading. For example, the variations in blood hematocrit level can in some circumstances cause variations in glucose measurements. To address the impedance issue, the test strip the present disclosure may further include an electrode system for an impedance measurement in the blood sample. The impedance measurement data may be used to correct the measurement of the analyte, i.e. glucose.

Figure 2:
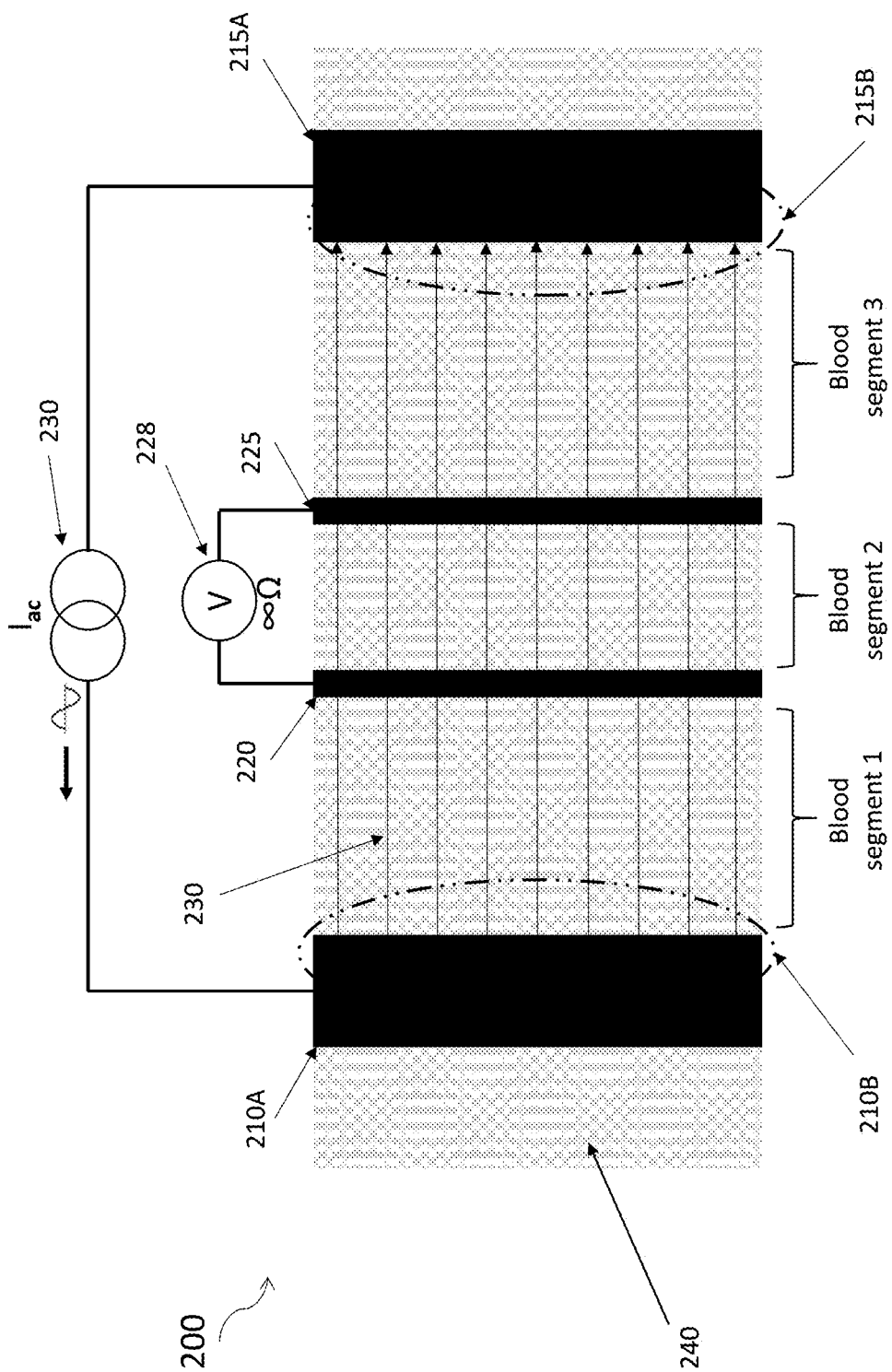
FIG. 2 illustrates a impedance measurement method, according to some embodiments of the present disclosure.

FIG. 2 illustrates a test strip having an impedance measurement method, according to some embodiments of the present disclosure. For example, at least one aspect of the impedance measurement method includes a first pair of electrodes (drive electrodes 210A & 215A) that imposes a precision AC current 230, e.g. a programmable (amplitude and frequency) alternating current source ($I_{ac}$), through a biological test sample, e.g. blood sample 240. The AC current 230 flows through the biological test sample 240 alternatively from one drive electrode 210A to the other drive electrode 215A as determined by a frequency of the precision current-source ($I_{ac}$) 230.

Still referring to FIG. 2, because the AC current amplitude can be determined (set) solely by the programmable precision current-source ($I_{ac}$) 230, it can be imposed on the entire impedance present between the drive electrodes 210A, 215A. A second pair of electrodes 220 & 225 (i.e. sense electrodes) can be physically located between the two drive electrodes 210A, 215A (i.e. measuring the impedance of blood segment 2), so that the current 230 flowing between the two drive electrodes 210A, 215A can also be flowing across the two sense electrodes 220, 225.

An electrode polarization impedance (EPI) 210B, 215B is present at the interface of each drive electrode 210A, 215A with the biological test sample 240. In some embodiments the two sense electrodes 220, 225 can be connected to a high input-impedance voltage measurement circuit to measure the difference in AC potential between them. The voltage measurement circuit having a high input-impedance can result in there being only a negligible current flowing between the sense electrodes 220, 225 and a voltmeter 228, e.g. a high impedance AC voltmeter that includes programmable amplitude and phase. As a result the sense electrodes 220, 225 may not be subject to electrode polarization impedance (EPI) 210B, 215B resulting from charge transfer, for example, due to a reduction in charge transfer between the sensing electrodes.

In some embodiments, with the voltage measuring circuit having a high input impedance, the tetrapolar system can be insensitive to changes in the electrode/sample impedance of the voltage-sensing electrodes. To that end, such insensitivity can be accomplished where the sensing electrodes may be directly connected to the high input impedance. As such, the impedance (e.g., impedance due to polarization of the sample/electrode interface) of the sensing electrodes may become negligible because such impedance may be in series with the high input impedance, where the high input impedance dominates the overall impedance value of the sensing section of the tetrapolar system and thereby minimizes the current going through the sensing electrodes.

Figure 3A:
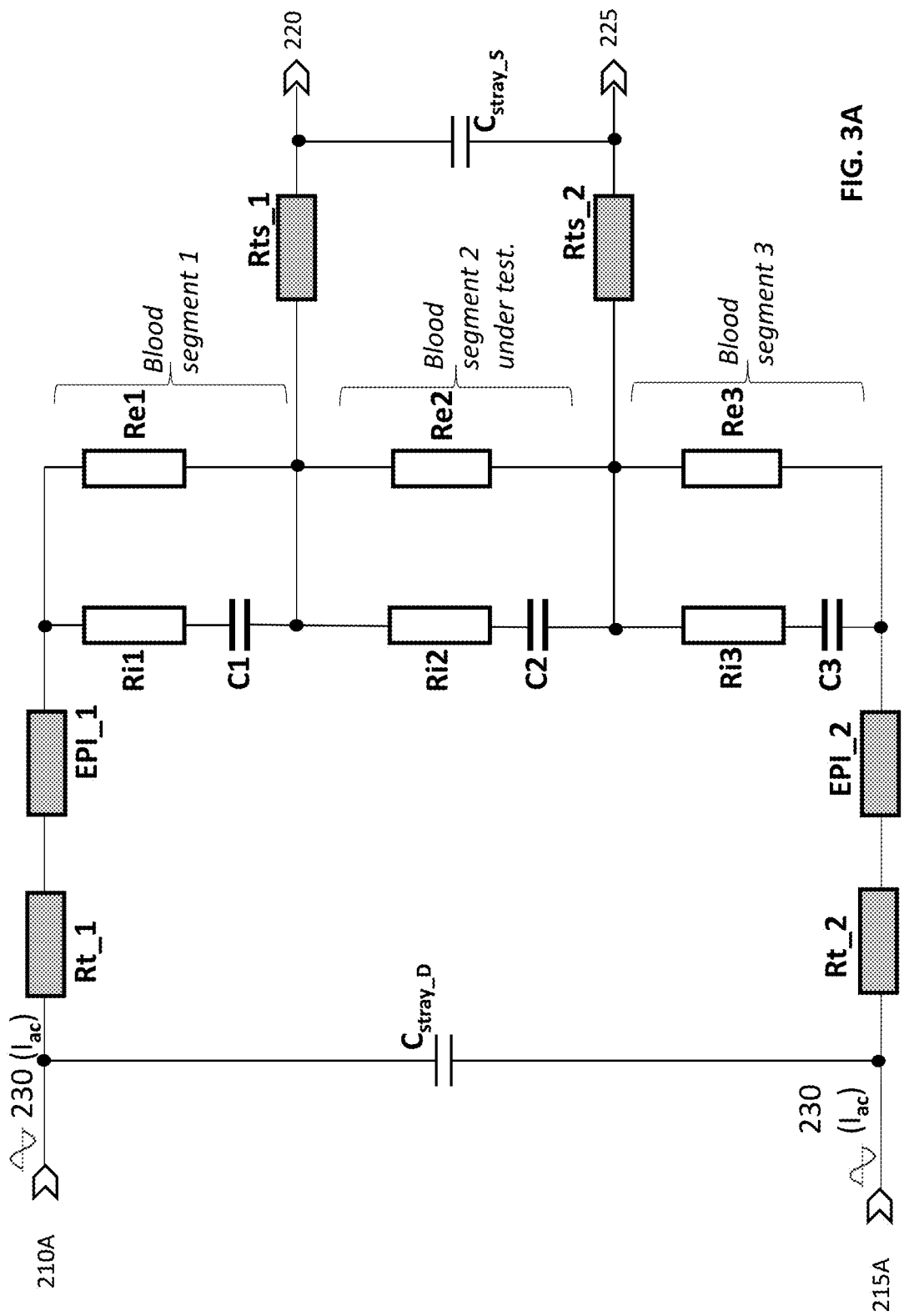
FIG. 3A illustrates an equivalent circuit of the circuit of FIG. 2, wherein the precision current-source ($I_{ac}$) current imposed by a current source enters an equivalent circuit via one of the two drive electrodes and exits via the other, according to some embodiments of the present disclosure.

FIG. 3A illustrates a similar circuit of the circuit of FIG. 2, wherein the precision current-source ($I_{ac}$) 230 imposed by a current source enters an equivalent circuit via one of the two drive electrodes 210A, 215A and exits via the other. For example, since the $I_{ac}$ current 230 is imposed by a current source, its amplitude is not dependent on the value of any Rt_x, EPI_x, Ri, Re or C elements. Wherein "C" represents cell membrane capacitance, "Ri" represents intra-cellular resistance, "Re" represents extra-cellular resistance, "$C_{stray\_x}$" represents strip parasitic capacitance and "EPI_x" represents electrode polarization impedance.

Further, the stray capacitance ($C_{stray\_D}$) between the drive electrodes 210A, 215A can influence the measurement if its effect is not mitigated, and at high frequency, it can have the potential of creating an alternative current path for a portion of $I_{ac}$ 230, thus introducing a frequency-dependent measurement error. It is noted that the depiction of $C_{stray\_D}$ capacitance is for the traces of the drive electrodes running parallel and adjacent to each other on the strip. Similarly, the stray capacitance $C_{stray\_S}$ effect which is frequency dependent and can influence the measurement. It is noted that the depiction of $C_{stray\_S}$ capacitance is for the traces of the sense electrodes running parallel and adjacent to each other on the strip. The methods and systems of the present disclosure may mitigate these effects.

Still referring to FIG. 3A, the sub-circuit actually under test (blood segment #2) can be subjected to the $I_{ac}$ current 230 (minus any current flowing through $C_{stray\_D}$ parasitic capacitance). For example, the blood segment #2 sub-circuit can be composed of: (1) Re2 representing the extra-cellular resistance (primarily resulting from the plasma resistivity); (2) Ri2 representing the intra-cellular resistance (primarily the aggregate internal resistance of the red blood cells); and (3) C2 representing the dielectric effect of the red blood cell membranes. The combination of Re2, Ri2 and C2 can form a complex impedance circuit producing an AC voltage between the two sense electrodes 220, 225 when $I_{ac}$ 230 is flowing.

The two sense electrodes 220, 225 can be connected to a high impedance circuit (differential AC voltmeter/phase detector) wherein a negligible current is flowing in the sense lines, i.e. between the two sense electrodes 220, 225. This negligible current can have important consequences, among other things. For example: (1) there can be no electrode polarization impedance affecting the two sense electrodes 220, 225; and (2) any voltage drop due to the trace resistance Rts_1 and Rts_2 will be negligible as well. The overall result of using a tetrapolar impedance measurement for a disposable test strip of the present disclose can be an improved hematocrit-specificity of the impedance measured between the sense lines, i.e. between the two sense electrodes 220, 225, as noted above.

Figure 3B:
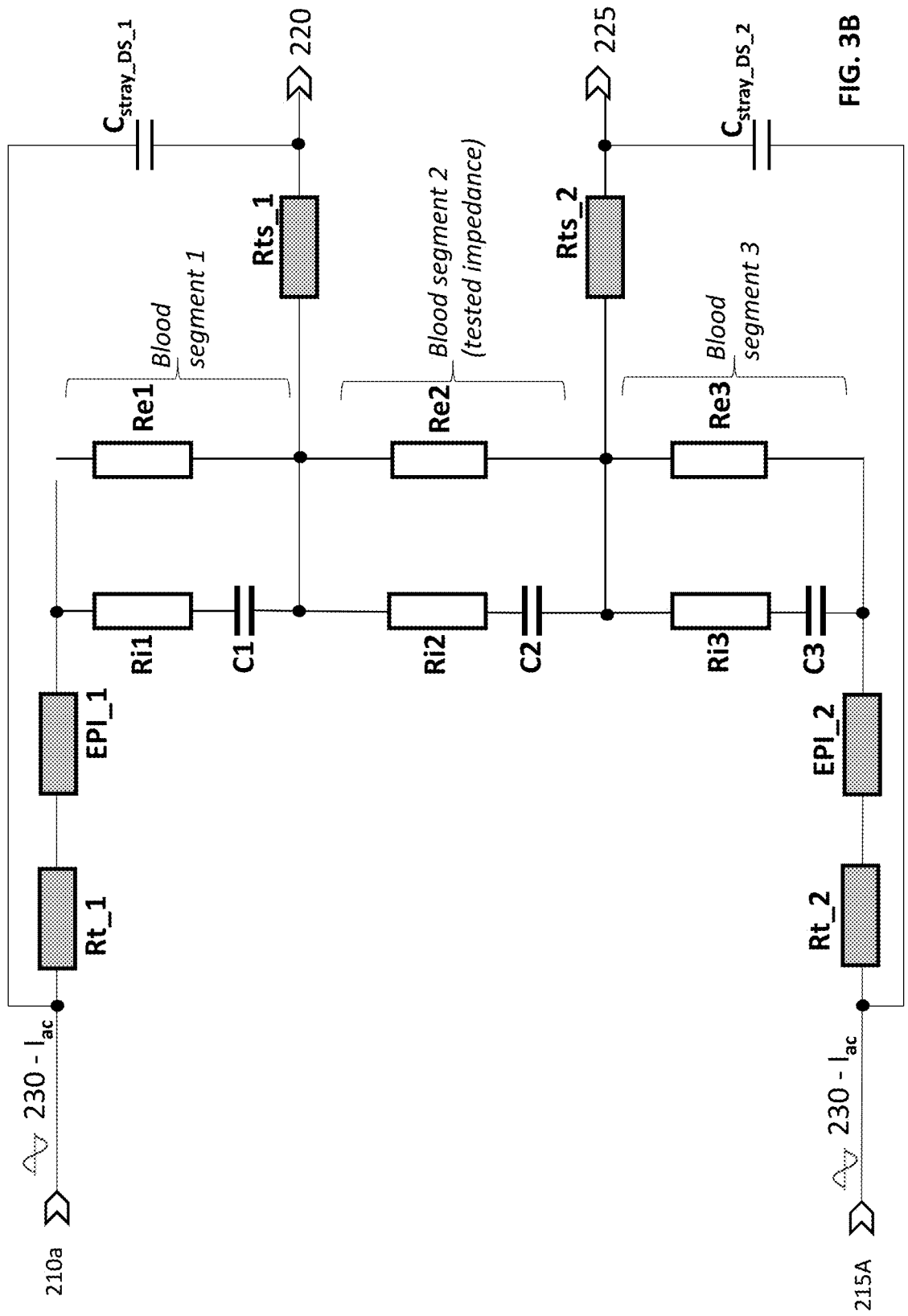
FIG. 3B illustrates an equivalent circuit of the circuit of FIG. 2, showing what happens to parasitic stray capacitances when the trace on the disposable strip of each sense electrode is purposely parallel and adjacent to the trace of the drive electrode closest to it in the capillary, according to some embodiments of the present disclosure.

FIG. 3B illustrates a similar circuit of the tetrapolar circuit of FIG. 2, showing what happens to parasitic stray capacitances when the trace on the disposable strip of each sense electrode 220, 225 is purposely parallel and adjacent to the trace of the drive electrode 210A, 215A closest to it in the capillary. For example, in this instance, stray capacitances become negligible between drive electrodes 210A, 215A or sense electrodes 220, 225 (see FIG. 3A), wherein they form parasitic bridges between each of the drive electrode 210A, 215A and the adjacent sense electrode 220, 225 ($C_{stray\_DS\_1}$ and $C_{stray\_DS\_2}$). The stray capacitances $C_{stray\_DS\_1}$ and $C_{stray\_DS\_2}$ are respectively in parallel with the impedance of blood segment 1 and blood segment 3, which doesn't prevent the entirety of the $I_{ac}$ current to flow through blood segment 2, as the impedance is being tested. Thus, when using a tetrapolar impedance configuration on a disposable glucose strip or the present disclosure, by purposely laying-out sense electrode traces so that they are adjacent to the traces of the drive electrode closest to each in the capillary, can significantly reduce phase and magnitude error at high frequency.

Further, in FIG. 3B, "C" represents cell membrane capacitance, "Ri" represents intra-cellular resistance, "Re" represents extra-cellular resistance, "Rt_x" represents strip parasitic trace resistance, "$C_{stray\_x}$" represents strip parasitic capacitance and "EPI_x" represents electrode polarization impedance. Further still, the depiction of $C_{stray\_DS1}$ capacitance is for the traces of the drive1 electrode 210A running parallel and adjacent to Sense1 electrode 220 on the strip. Also, the depiction of $C_{stray\_DS2}$ capacitance is for the traces of the drive2 electrode 215A running parallel and adjacent to Sense2 electrode 225 on the strip.

Figure 4B:
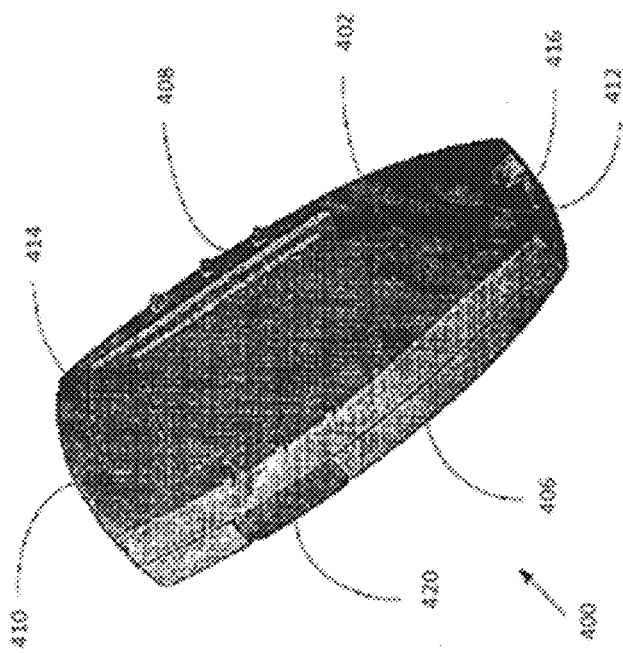
FIGS. 4A and 4B illustrates a meter, according to some embodiments of the present disclosure.
Figure 4A:
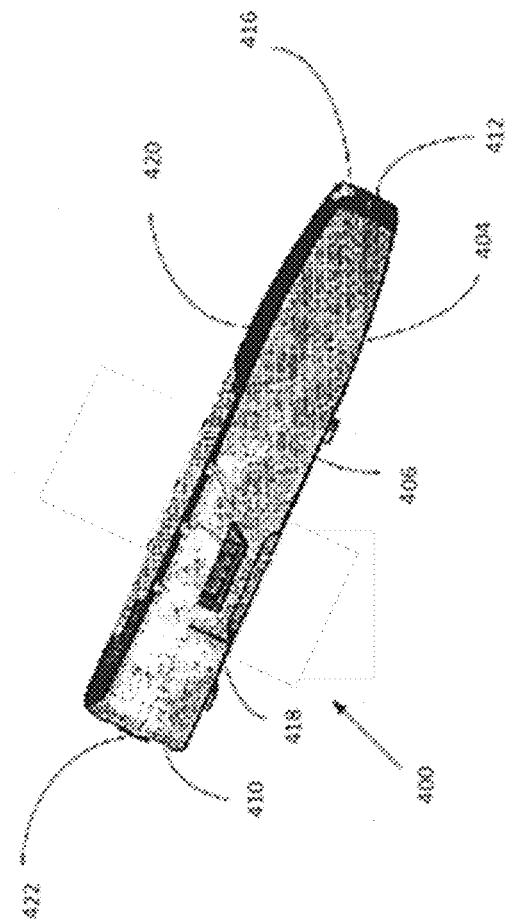

FIG. 4A and FIG. 4B illustrates a meter 400 used to measure the glucose level in a blood sample. In some embodiments, the meter 400 has a size and shape to allow it to be conveniently held in a user's hand while the user is performing the glucose measurement. Meter 400 may include a front side 402, a back side 404, a left side 406, a right side 408, a top side 410, and a bottom side 412. The front side 402 may include a display 414, such as a liquid crystal display (LCD). A bottom side 412 may include a strip connector 416 into which test strip can be inserted to conduct a measurement.

Referring to FIG. 4A and FIG. 4B, the left side 406 of meter 400 may include a data connector 418 into which a removable data storage device 420 may be inserted, as necessary. The top side 410 may include one or more user controls 422, such as buttons, with which the user may control meter 400, and the right side 408 may include a serial connector (not shown).

FIG. 5A illustrates a top perspective view of a test strip 510 inserted within a meter connector 530 consistent with the present invention. Test strip 510 includes a proximal electrode region 524, which contains the capillary chamber and measuring electrodes, as described above. Proximal electrode region 524 may be formed to have a particular shape in order to distinguish to the user the end receiving a fluid sample from distal strip contact region 526. Meter connector 530 includes channel 532 extending out to a flared opening for receiving the test strip 510. Meter connector 530 may further include tangs 536 extending a predetermined height above the base of channel 532. The predetermined height of tangs 536 is selected to limit the extent, such as through a corresponding raised layer of test strip 510, to which a test strip 510 can be inserted into channel 532. Meter connector 530 may include a first plurality of connector contacts 538, disposed closer to the proximal end of meter connector 530, which are configured to contact the electrical strip contacts 519 upon insertion of the test strip 510 into the meter connector 530. In some embodiments, the test strip control circuit reader 540 may be disposed closer to the distal end of meter connector 530 to communicate with the test strip control circuit 550. In some embodiments, the meter may be provided with one or more GPIO lines for communication with the IC. The one or more GPIO lines may replace digital coding lines (typically 3-5) utilizing GPIOs.

FIG. 5B illustrates a general cross-sectional view of a test strip inserted within meter connector 530 of FIG. 5A, consistent with the present invention. Channel 532 depicts a proximal row of connectors comprising a plurality of connector contacts 538 for connection the electrical strip contacts 519 upon insertion of the test strip 510 into the meter connector 530.

Figure 6:
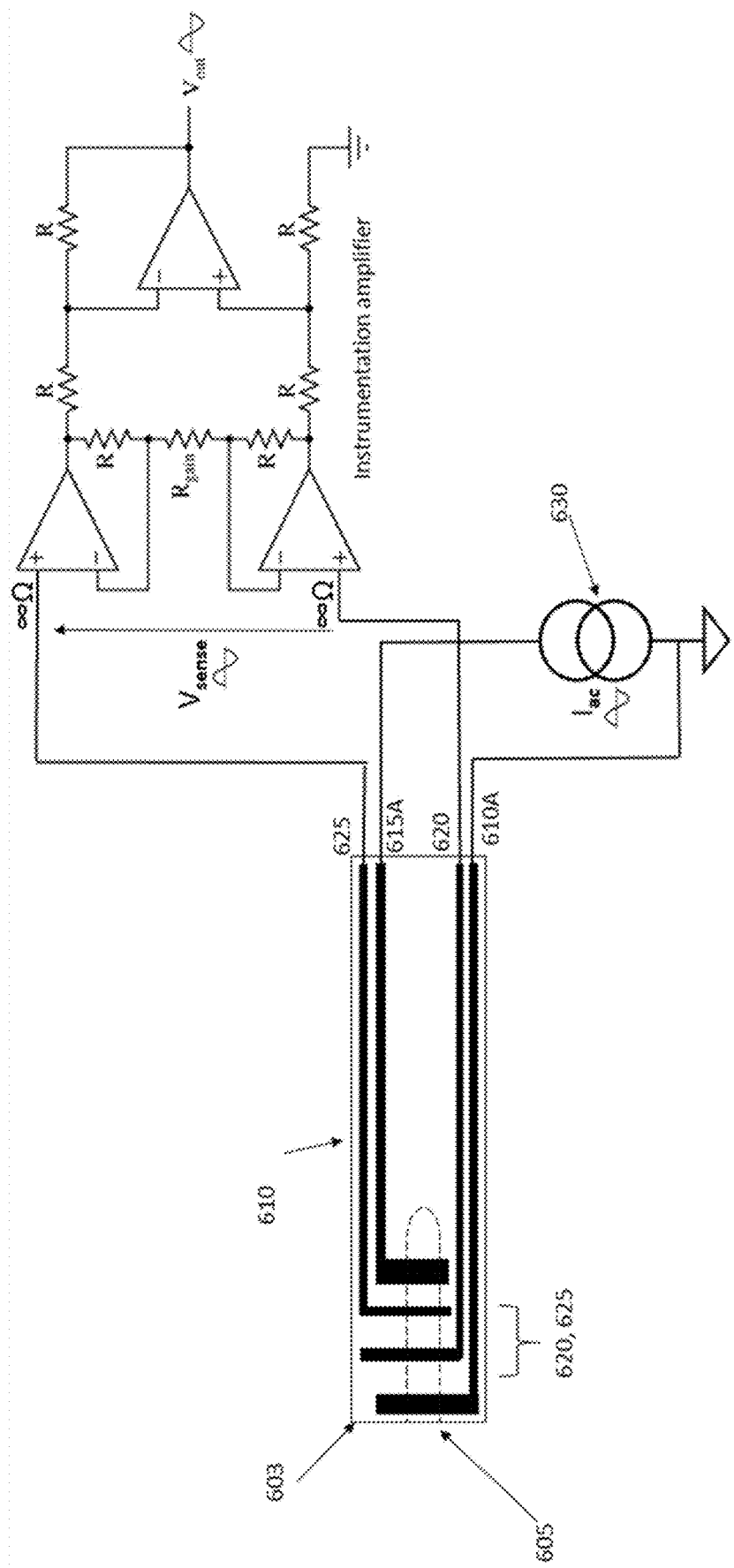
FIG. 6 illustrates a schematic of a test strip equipped with tetrapolar electrodes and analog front end (AFE) building blocks it connects to, according to some embodiments of the present disclosure.

FIG. 6 illustrates a schematic of a test strip 610 equipped with tetrapolar electrodes and analog front end (AFE) building blocks it connects to. For example, a capillary 605 located at the distal end 603 of the test strip 610 is filled with a blood sample; a proper fill ensures that all four (4) electrodes 610A, 615A, 620, 625 are covered by the test sample. The sense electrodes pair 620, 625 is located in-between the drive electrodes 610A, 615A. The glucometer AFE provides an instrumentation amplifier (or a buffered differential amplifier). The instrumentation amplifier inputs connected to the sense lines present an extremely high resistance ($\infty \Omega$ on FIG. 6) to the sense electrodes. The programmable current source is connected to the drive electrodes 610A, 615A. The instrumentation amplifier connected to the sense electrodes 620, 625 amplifies the difference in voltage between them, while rejecting any signal common to both (common-mode rejection). It is noted that the trace of drive electrode 210A running parallel and adjacent to sense electrode 220, and trace of drive electrode 215A running parallel and adjacent to sense electrode 225 to, for example, eliminate or reduce the stray capacitances, by creating a capacitance bridge between the driving electrodes.

Figure 7:
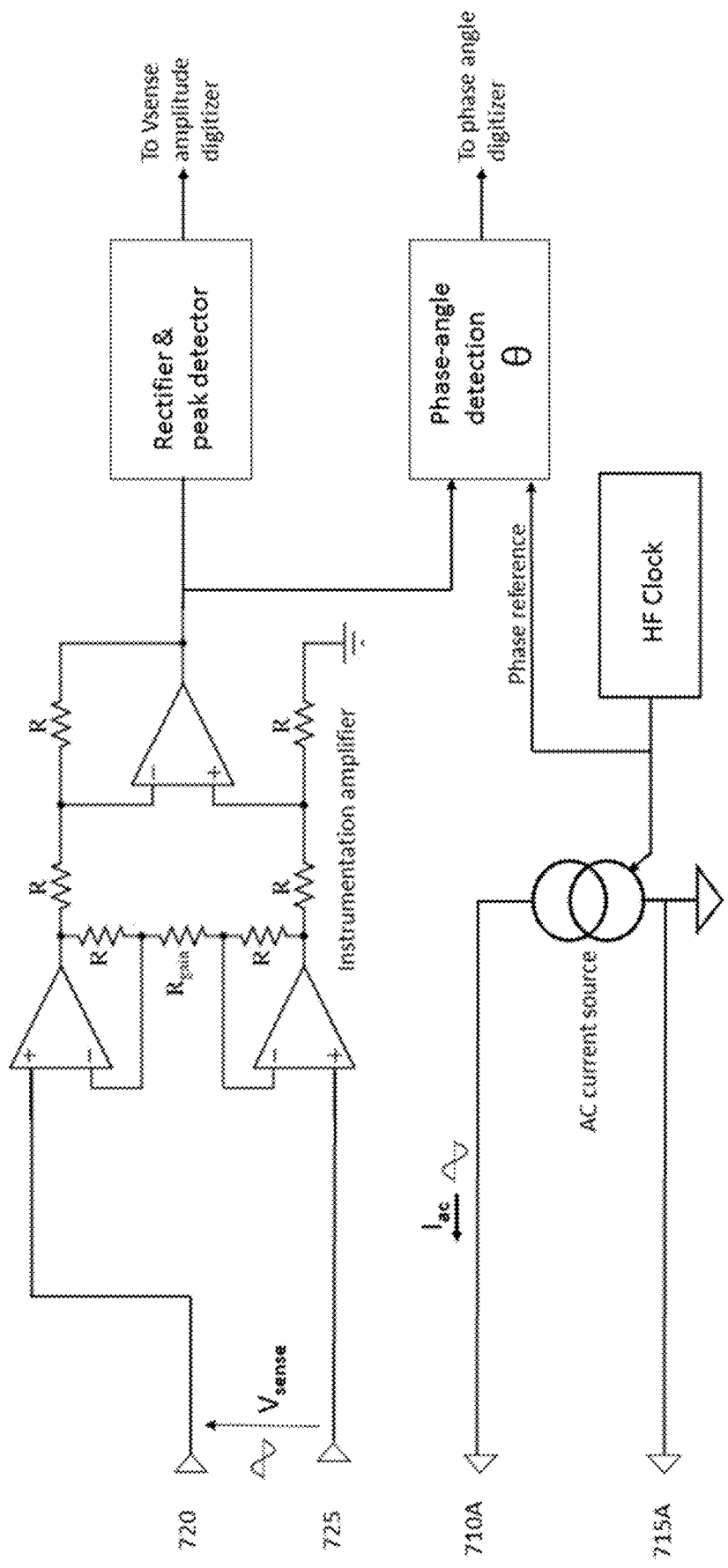
FIG. 7 illustrates an output of an instrumentation amplifier coupled to other circuitry such as a rectifier, integrator and analog-to-digital converter in order to obtain a digital value for a voltage amplitude, according to some embodiments of the present disclosure.

FIG. 7 illustrates an output of an instrumentation amplifier coupled to other circuitry such as a rectifier, integrator and analog-to-digital converter in order to obtain a digital value for a voltage amplitude. For example, both the output of the instrumentation amplifier and the current source (phase reference) can be coupled to a phase-angle detection circuit, wherein itself can be coupled to a digitizer. It is understood that FIG. 7 is for illustration purposes only and that the signal processing of AC voltage and current can take many forms including hardware and/or firmware, depending on the type of signal processing approach selected for detailed implementation. Further, FIG. 7 shows the sense electrodes 720, 725 and the drive electrodes in the schematic.

Figure 8:
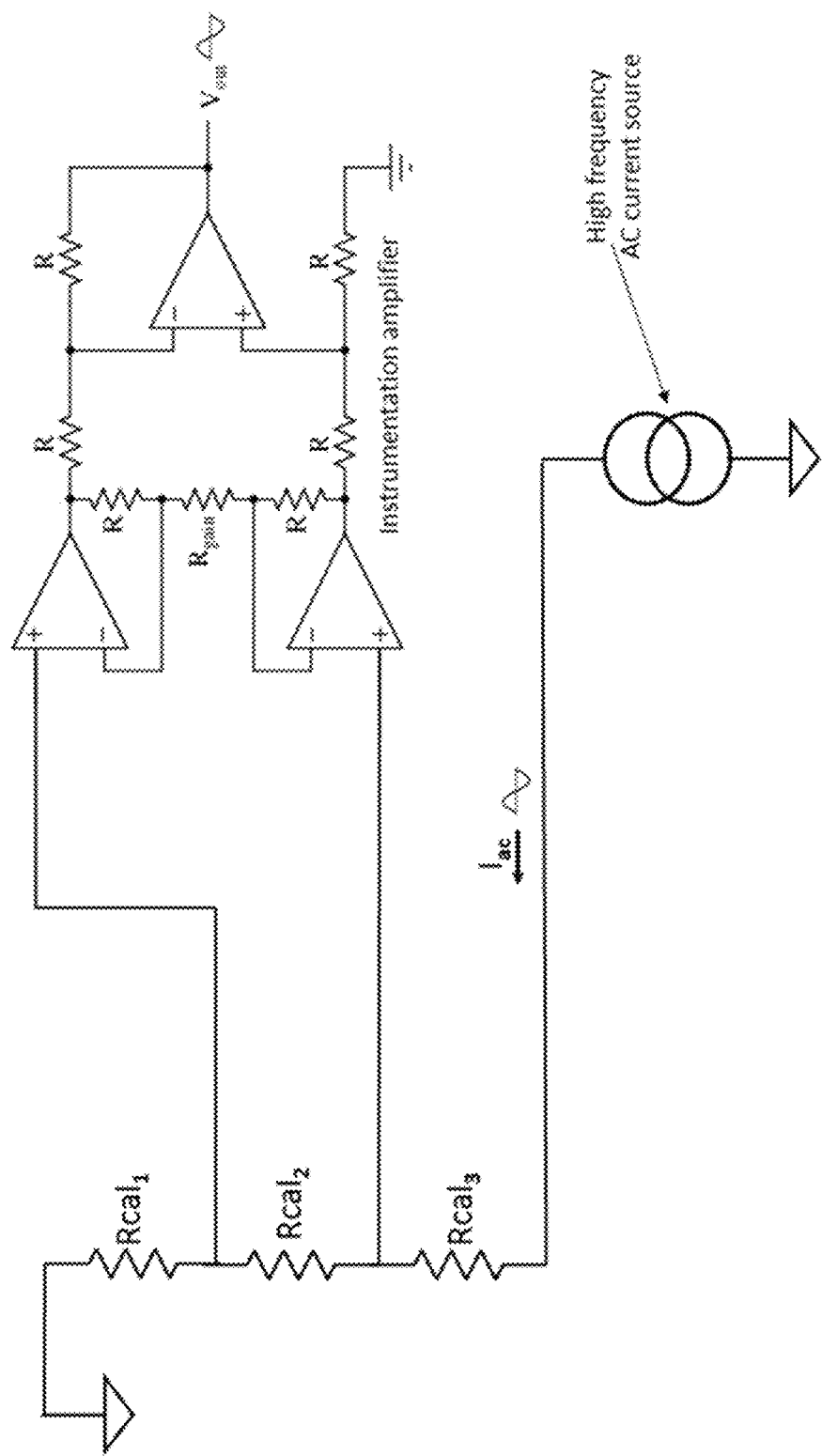
FIG. 8 and FIG. 9 illustrate how precise calibration components (Rcalx, Ccalx) located within a glucometer can be temporarily connected between a current source and an instrumentation amplifier (instead of the measurement electrodes) in order to calibrate an analog front-end, according to some embodiments of the present disclosure.
Figure 9:
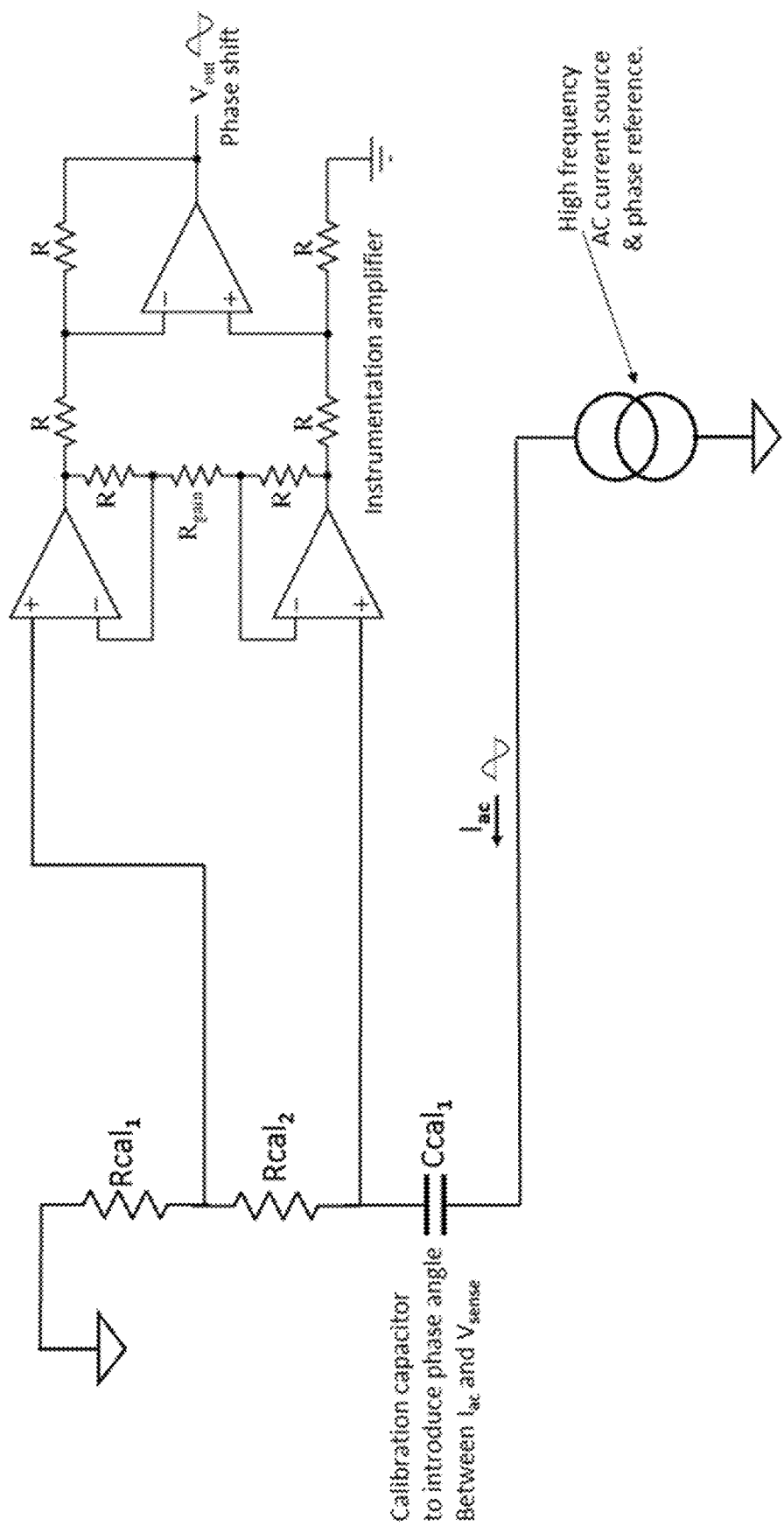

FIG. 8 and FIG. 9 illustrate how precise calibration components (Rcalx, Ccalx) located within a glucometer can be temporarily connected between a current source and an instrumentation amplifier (instead of the measurement electrodes) in order to calibrate an analog front-end. For example, this calibration can cover a range of current source amplitudes and frequencies in order to carry-out a multiple point's calibration over the entire operating range of the AFE.

Figure 10A:
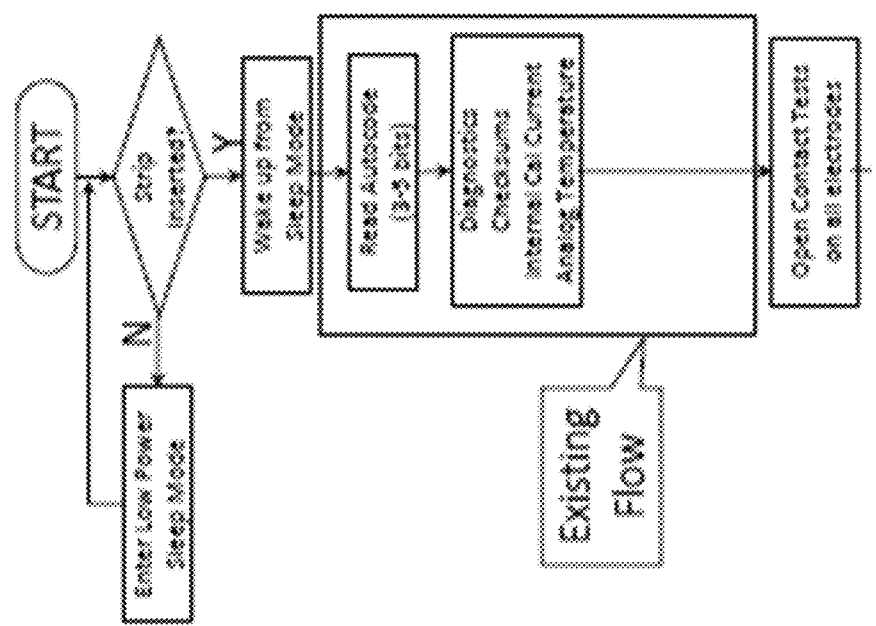
FIG. 10A and FIG. 10B present a flow chart showing a test routine, according to some embodiments of the present disclosure.
Figure 10B:
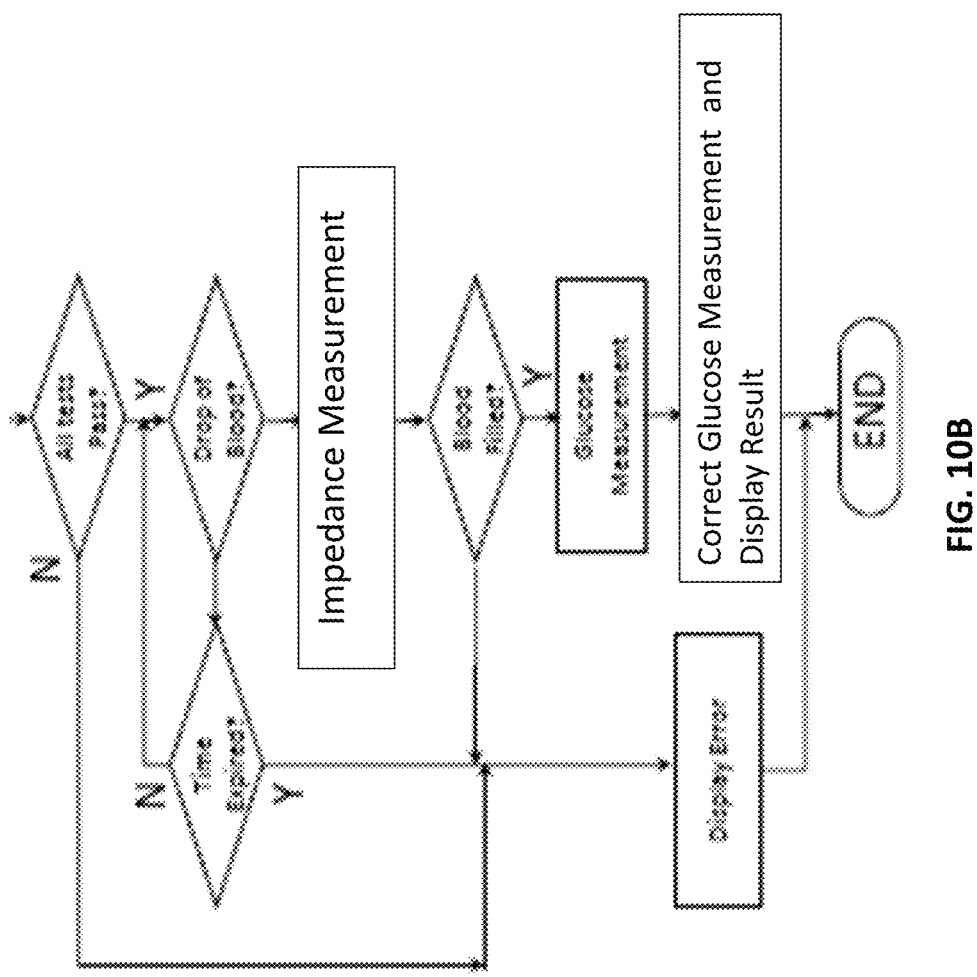

FIG. 10A and FIG. 10B present a flow chart showing a test routine, according to some embodiments of the present disclosure. For example, FIG. 10A shows that the meter may be battery powered and may stay in a low-power sleep mode when not in use in order to save power. When the test strip is inserted into the meter, current flow to the meter causes the meter to wake up and enter an active mode. Alternatively, the meter may be provided with a wake button.

Referring to FIG. 10A, next, the meter can connect to the control circuit to read the code information from the control circuit and can then identify, for example, the particular test to be performed, or a confirmation of proper operating status. In addition, the meter can also identify the inserted strip as either a test strip or a check strip based on the particular code information. If the meter detects a check strip, it performs a check strip sequence. If the meter detects a test strip, it performs a test strip sequence.

Still referring to FIG. 10A, in addition, the meter can ensure that the test strip is authentic and has not been previously used. The meter will also read the temperature of the test strip. Diagnostics may include checksums or cyclic redundancy checks (CRC) of portions of the internal and/or external memory to establish confidence that the memory is not corrupted because the checksum/crc data calculated matches the programmed checksum/crc. Another diagnostics test that may be performed is an LCD test to verify the integrity of the LCD to gain confidence it is not cracked and will display the proper result to the user that is sent to it. Another diagnostic test that may be performed is an internal calibration current test to verify that the analog front end continues to measure an accurate current within the margin of error allowed.

Still referring to FIG. 10A, if all information checks out, the meter can perform open contact tests on all electrodes to validate the electrodes. The meter may validate the electrodes by confirming that there are no low-impedance paths between any of these electrodes. If the electrodes are valid, the meter indicates to the user that sample may be applied to the test strip and the meter can perform analyte measurements.

Referring to FIG. 10B, next, to detect that an adequate sample is present in the capillary chamber and that the blood sample has traversed the reagent layer and mixed with the chemical constituents in the reagent layer, the meter may apply a fill-detect voltage between the fill-detect electrodes and measure any resulting current flowing between the fill-detect electrodes. If this resulting current reaches a sufficient level within a predetermined period of time, the meter indicates to the user that adequate sample is present and has mixed with the reagent layer. The meter can be programmed to wait for a predetermined period of time after initially detecting the blood sample, to allow the blood sample to react with the reagent layer or can immediately begin taking readings in sequence. In one example, the reagent layer may react with glucose in the blood sample in order to determine the particular glucose concentration. It should be noted that while the operation of the system of the present disclosure has been described primarily in connection with determining glucose concentration in blood, the systems of the present disclosure may be configured to measure other analytes in blood as well as in other fluids, as discussed above.

The meter may also measure impedance of the blood sample (such as due to hematocrit variations) which may interfere with the glucose measurement. The meter may later use such information to adjust the glucose concentration measurement to account for the impedance in blood.

In one example, the reagent layer may react with glucose in the blood sample in order to determine the particular glucose concentration. In one example, glucose oxidase is used in the reagent layer. The recitation of glucose oxidase is intended as an example only and other materials can be used without departing from the scope of the invention. Other possible mediators include, but are not limited to, ruthenium and osmium. During a sample test, the glucose oxidase initiates a reaction that oxidizes the glucose to gluconic acid and reduces the ferricyanide to ferrocyanide. When an appropriate voltage is applied to a working electrode, relative to a counter electrode, the ferrocyanide is oxidized to ferricyanide, thereby generating a current that is related to the glucose concentration in the blood sample. The meter then calculates the glucose level based on the measured current and on calibration data that the meter has been signaled to access by the code data read from the second plurality of electrical contacts associated with the test strip. The meter can then correct the glucose concentration based on the impedance measurement and displays the corrected glucose level to the user.

In some embodiments, as noted above, the test strip meter comprises a decoder for decoding a predetermined electrical property, e.g. resistance, from the test strips as information. The decoder operates with, or is a part of, a microprocessor. Wherein the meter can be programmed to wait for a predetermined period of time after initially detecting the blood sample, to allow the blood sample to react with the reagent layer or can immediately begin taking readings in sequence. During a fluid measurement period, the meter applies an assay voltage between the working and counter electrodes and takes one or more measurements of the resulting current flowing between the working and counter electrodes. The assay voltage is near the redox potential of the chemistry in the reagent layer, and the resulting current is related to the concentration of the particular constituent measured, such as, for example, the glucose level in a blood sample.

Figure 11:
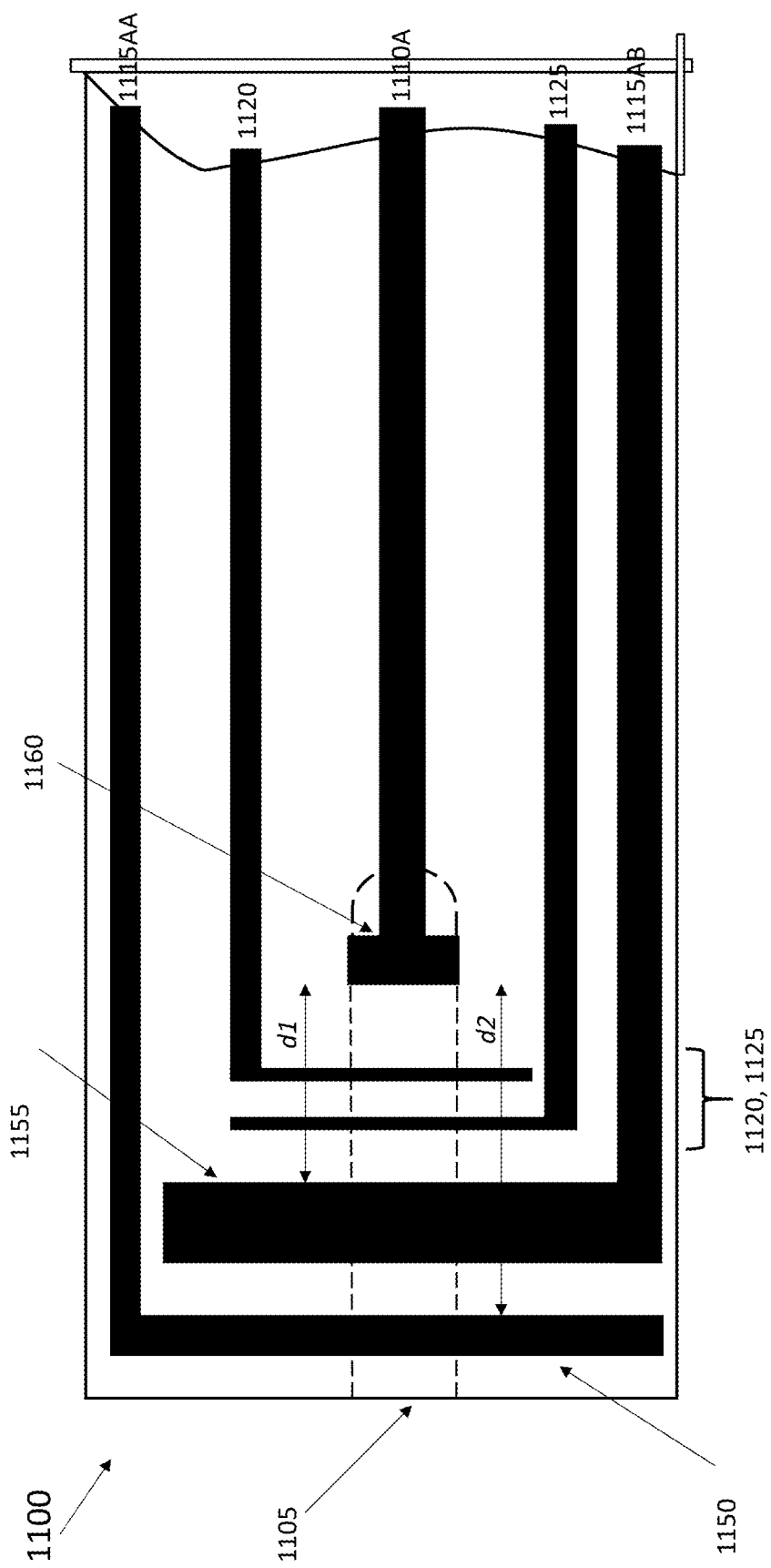
FIG. 11 illustrates a disposable strip including a glucose anode at a distal end of a capillary, followed by a glucose cathode, two sense electrodes, and a "fill-detect" electrode at a proximal end of the capillary, according to some embodiments of the present disclosure.

FIG. 11 illustrates a disposable strip 1100 including a glucose anode 1150 at a distal end of a capillary 1105, followed by a glucose cathode 1155, two sense electrodes 1120, 1125, and a "fill-detect" electrode 1160 at a proximal end of the capillary 1105. For example, the fill-detect electrode 1160 can be assigned the drive electrode 1110A secondary function (hematocrit test AC current injection)

and either the glucose anode 1150 or the glucose cathode 1155 can be assigned the hematocrit test current return secondary function. FIG. 11 uses the drive electrodes (i.e. designators) 1115AA and 1115AB to illustrate the fact that with this particular strip configuration two possible paths exist for the test current. Further, by having the ability to select among different sets of drive electrodes 1110A, 1115AA, 1115AB at least one aspect includes that it can be utilized by the glucometer AFE and associated firmware, in order, to dynamically select the optimum ratio between the sense electrodes distance (fixed) and the drive electrodes distance (selectable between d1 and d2).

Figure 12:
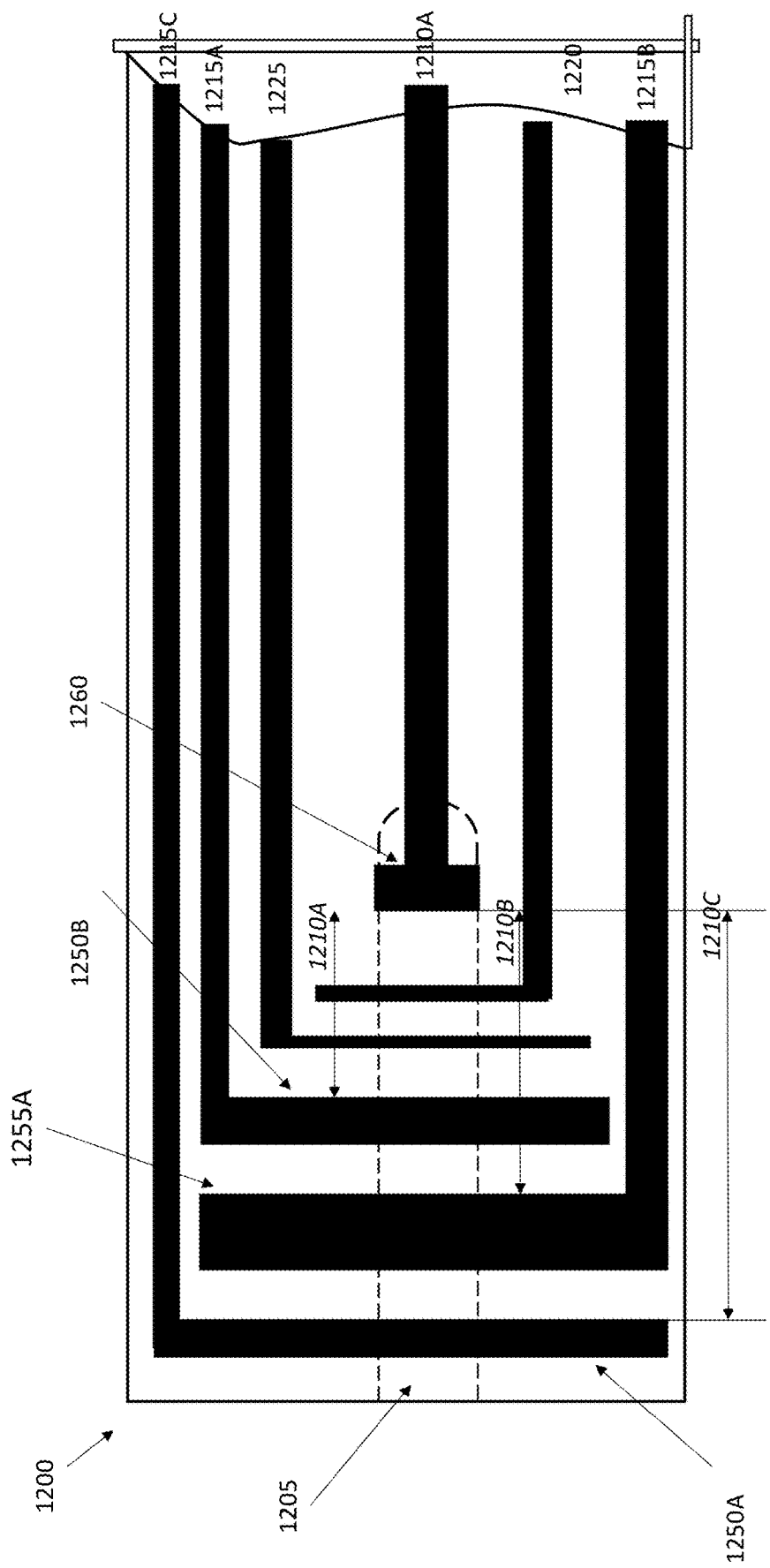
FIG. 12 illustrates a derivative of FIG. 11, wherein the strip includes a second glucose anode, i.e. a first anode and a second anode covered with different reagents, according to some embodiments of the present disclosure.

As FIG. 12 illustrates in some embodiments, the strip 1200 includes a second glucose anode, i.e. a first anode 1250A and a second anode 1250B covered with different reagents. For example, this particular strip 1200 can be equipped with a second glucose anode (anode 1, 1255A and anode 2, 1255B that can be covered with different reagents). In this instance, with the drive electrode 1110A the current injection function still is assigned to the fill-detect electrode 1260, a total of three (3) potential return paths can exist for the test current: (1) a first glucose anode 1250A; (2) a second glucose anode 1250B; and (3) a glucose cathode 1255A. It is noted that this triple return path can be used by the AFE and associated firmware to dynamically select a desired ratio between the sense electrodes distance (fixed) and the drive electrodes distance (selectable between d1, d2 and d3).

As shown in FIG. 11 and FIG. 12 the exact distance between the drive electrodes (d1, d2 or d3 as shown) 1210A, 1210B and 1210C, that is: the distance between the fill-detect electrode and the other electrode used for current injection purposes may be varied as it is not critical to measurement accuracy since the current is imposed (set) by the glucometer current source and not directly dependent on the distance between drive electrodes, among other things. The dimensional tolerance of the distance between drive electrodes may be configured without affecting the impedance measurement of the disposable glucose strip. Further, FIG. 12 shows second drive electrodes 1215A, 1215B and 1215C. Further, in spite of the fact that there is essentially no current (or negligible current) flowing between the sense electrodes 1220, 1225 and the AFE, the possibility exist that the flow of current over each sense electrode (in particular if they are sufficiently wide) could be enough by itself to elicit potentially some degree of electrode polarization. For this reason, the sense electrodes 1220, 1225 may be made as narrow as possible and it is not necessary to give them the full width of the capillary, among other aspects. According to at least one aspect of making the sense electrodes as narrow as possible is also consistent with design objectives of glucose strips since narrow electrodes implies a shorter capillary, and thus less blood volume required for a test.

Figure 13:
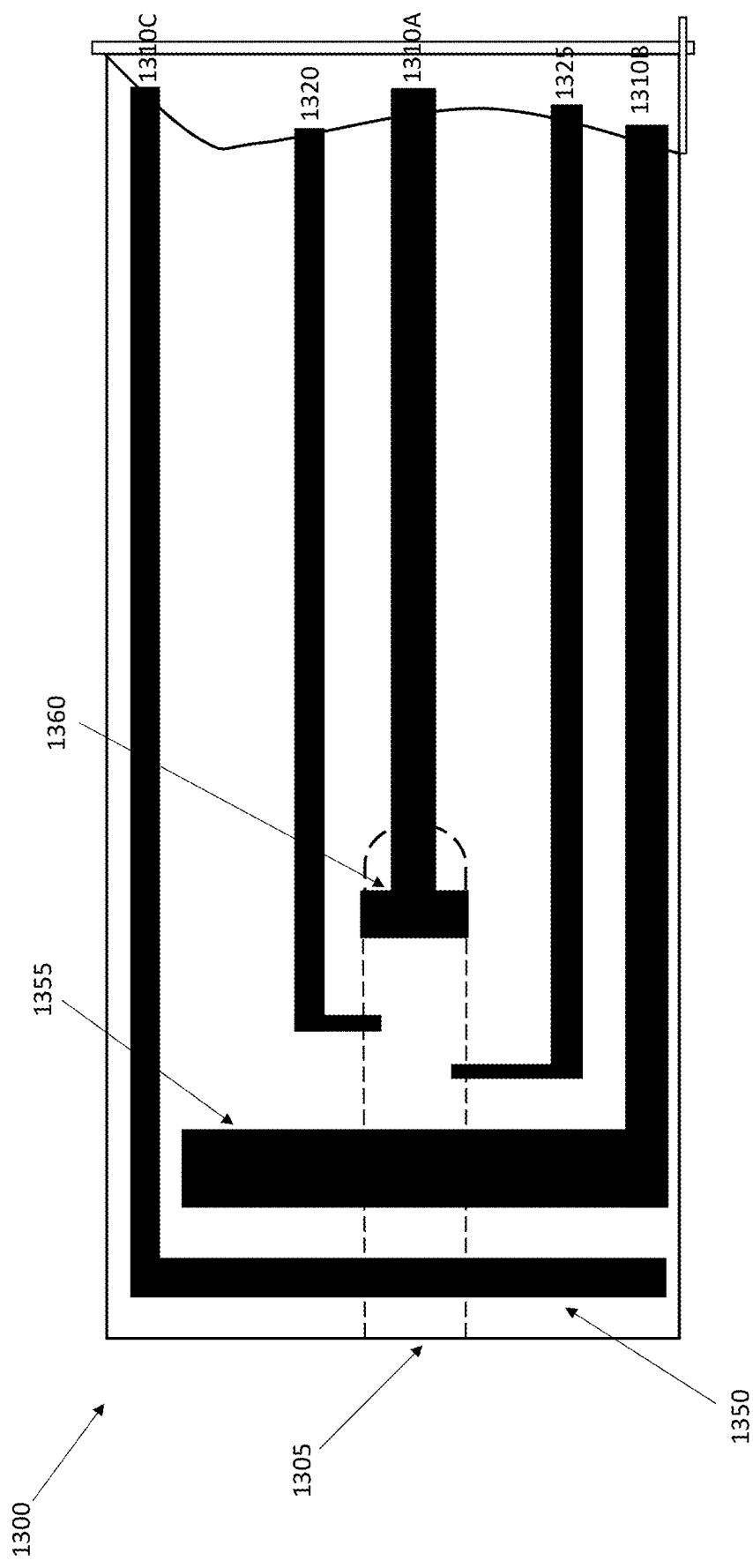
FIG. 13 and FIG. 14 illustrate derivatives of FIG. 11, wherein an exact distance between the drive electrodes (d1, d2 or d3), that is: the distance between a fill-detect electrode and another electrode used for current injection purposes is not critical to measurement accuracy due to the current being imposed (set) by a glucometer current source and not directly dependent on a distance between drive electrodes, according to some embodiments of the present disclosure.
Figure 14:
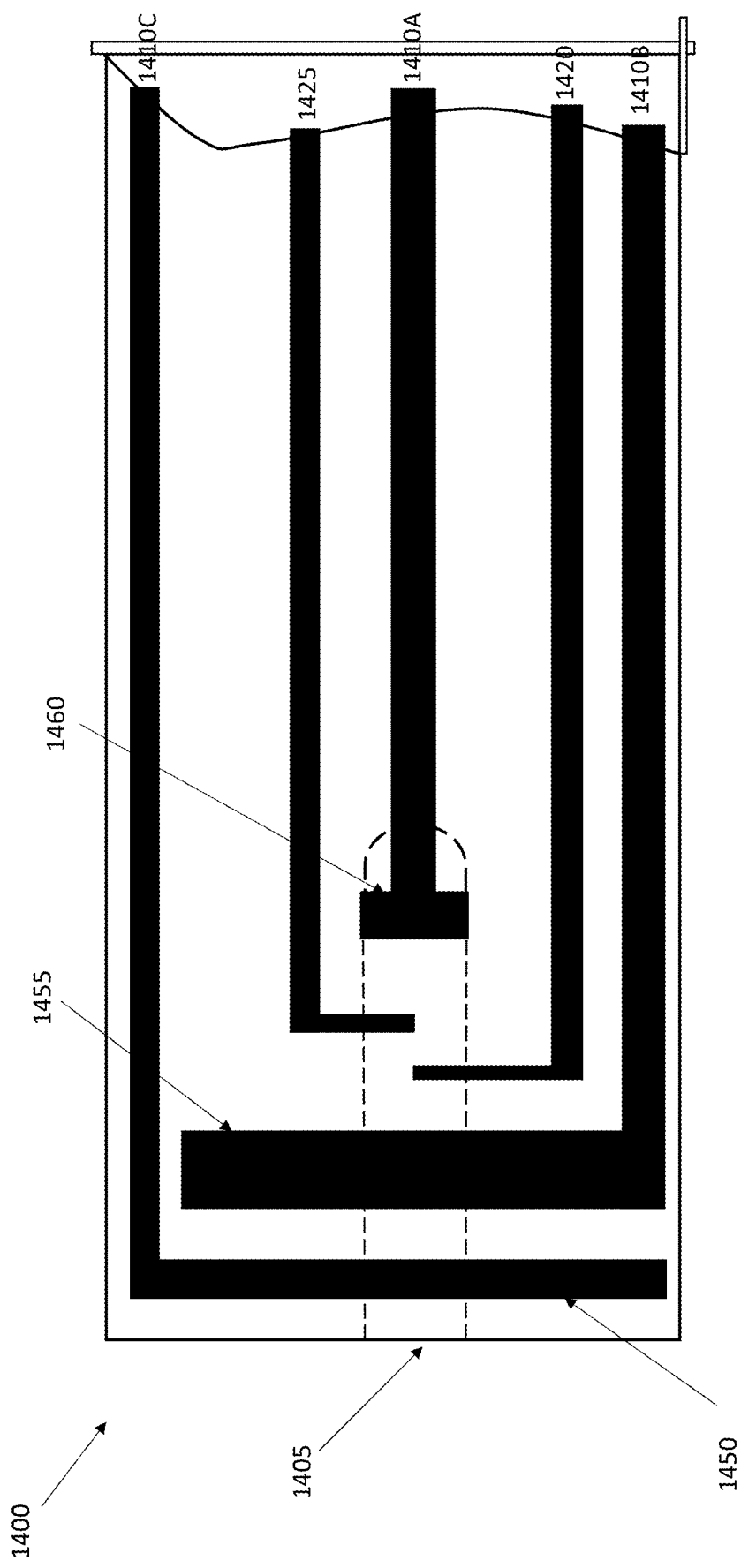

FIG. 13 and FIG. 14 illustrate derivatives of FIG. 11, showing that it is possible with short sense electrodes which are sufficiently exposed to the blood to capture the voltage at their location, are also short and narrow enough to minimize polarization effect due to their length. FIG. 13 illustrates in some embodiments, the strip 1300 includes a glucose anode 1350, a glucose cathode 1355 and a capillary 1305. In this instance, with the Drive-1 current injection function still assigned to the fill-detect electrode 1360, a total of two (s) potential return paths can exist for the test current: (1) a glucose anode, 1350; and (2) a glucose cathode 1355. Further, FIG. 13 shows drive electrodes 1310A, 1310B and 1310C, as well as sense electrodes 1320, 1325.

FIG. 14 illustrates in some embodiments, the strip 1400 includes a glucose anode 1450, a glucose cathode 1455 and a capillary 1405. In this instance, with the drive-1 current injection function still assigned to the fill-detect electrode 1460, a total of two (s) potential return paths can exist for the test current: (1) a glucose anode, 1450; and (2) a glucose cathode 1455. Further, FIG. 14 shows drive electrodes 1410A, 1410B and 1410C, as well as sense electrodes 1420, 1425.

Figure 15:
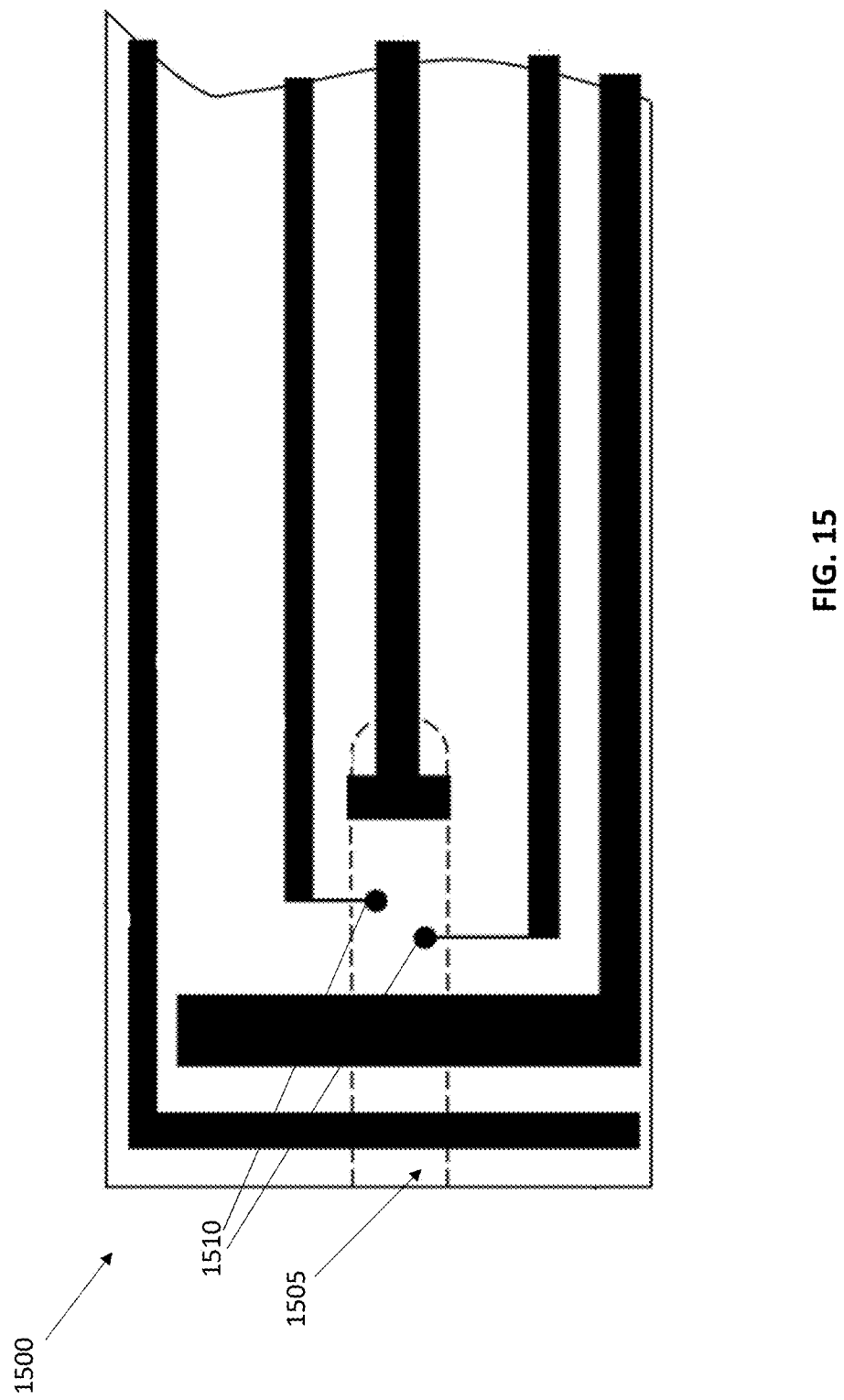
FIG. 15 and FIG. 16 illustrate embodiments of a test strip of the present disclosure.

FIG. 15 illustrates in some embodiments, the strip 1500 can include thin traces leading into a fixed size electrode for hematocrit sensing. It should be noted that the size of the electrodes 1510 can be a contributing factor to various measurements. For example, thin lines leading into a fixed size electrode can allow the placement of a reaction well 1505 to move up and down within the strip 1500, thereby providing additional manufacturing robustness to the strip 1500 design. Furthermore, in some embodiments, various geometric shapes can be used to form the electrodes 1510, so long as the shape provides optimal accuracy and efficiency to the various hematocrit and/or glucose measurements, as well as making the manufacturing of the strip 1500 more robust. For example, the electrodes 1510 can be made to be circular in shape to provide the optimal shape for a given surface area.

Figure 16:
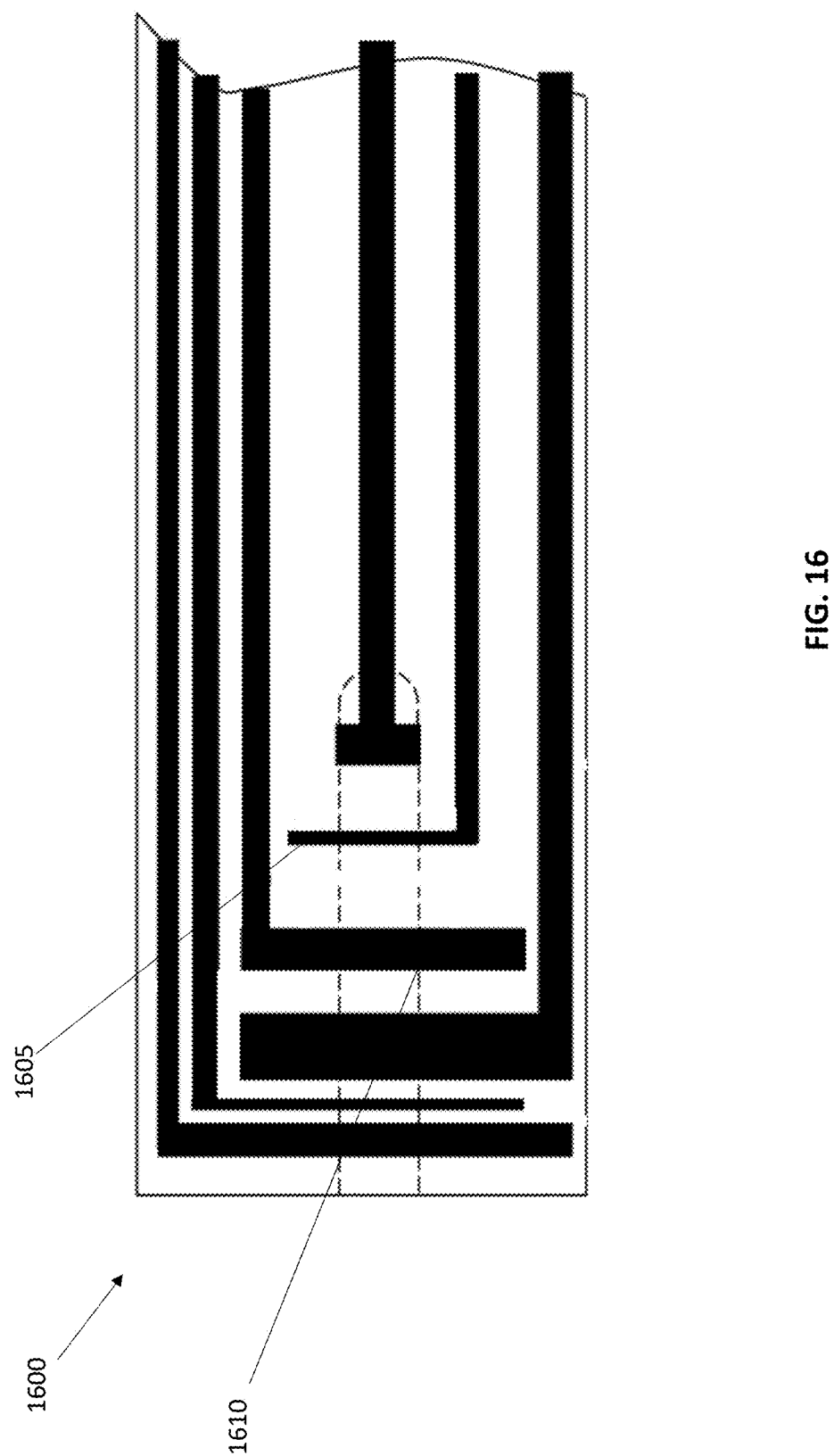

FIG. 16 illustrates that, in some embodiments, the strip 1600 can include sensing electrodes 1605, 1610 that are further apart from each other to, for example, improve manufacturing robustness of the strip 1600. For example, electrode distances variations due to manufacturing imperfections can lead to measurement reading variations. To that end, increasing the distance between the electrodes 1605, 1610 can minimize that effect and thus improve manufacturing robustness of the strip 1600. In some embodiments, signals used for the drive electrodes can be such that the signal poses minimal or no influence on the strip 1600 reagents and/or the analyte(s) being measured if there were reagents covering one or both of the sensing electrodes 1605, 1610. Furthermore, in some embodiments, during chemical deposition process of the manufacturing of the strip 1600, the electrodes can optionally not be covered with reagents.

In some embodiments, an AC measurement and/or a DC measurement may be used and the hematocrit measurements may be calculated by way of subtraction.

According to aspects of the present disclosure, there can be alternate embodiments of the present disclosure. For example, some embodiments may include a disposable test strip for an electrochemical biosensor equipped with at least four (4) electrodes within a capillary channel forming a AC impedance sensor, with 2 electrodes used to inject an AC current between them, said current programmable in amplitude and frequency and two (2) sensing electrodes physically adjacent to each other within the capillary and positioned in-between the drive electrodes, the disposable test strip coupled to an instrument producing the AC current and processing the signals from the sense electrodes.

According to aspects of the present disclosure, an impedance measurement can have an additional pair of electrodes to what is typically implemented on a strip that uses a single pair of electrodes. However, more electrodes can mean more points of interface with the glucometer strip connector, which can lead to a more complex ablation of metal on the strip and thus the potential for lower production yields. At least one aspect to address this issue can be to assign a plurality of functions to existing (analyte) electrodes.

According to some embodiments of the present disclosure, the embodiment may include a disposable test strip for an electrochemical biosensor equipped with at least four (4)

electrodes within a capillary channel forming a AC impedance sensor at the distal end of the test strip, with connector pad at the proximal end of said test strip and conductive traces between proximal and distal end laid-out such that each current injecting trace is parallel and adjacent to the sense trace closest to it within the capillary.

According to some embodiments of the present disclosure, the embodiment may include a disposable test strip for an electrochemical biosensor equipped with at least four (4) electrodes within a capillary channel forming a tetrapolar AC impedance sensor, the strip designed to be electrically and mechanically coupled to an instrument injecting a preset AC current between two (2) of the electrodes, and receiving the signal of the other two electrodes a differential or instrumentation amplifier.

According to some embodiments of the present disclosure, the embodiment may include a disposable test strip for an electrochemical biosensor equipped with at least four (4) electrodes within a capillary channel forming a AC impedance sensor at the distal end of the test strip and such that the electrodes used to inject the AC current through the sample contained within the capillary also serve the purpose to measure one or more electrochemical analyte also contained within said capillary.

According to some embodiments of the present disclosure, the embodiment may include a disposable test strip for an electrochemical biosensor equipped with at least four (4) electrodes within a capillary channel forming a AC impedance sensor at the distal end of the test strip and such that the electrodes used to inject the AC current through the sample contained within the capillary also serve the purpose to measure one or more electrochemical analyte also contained within said capillary within the analyte measurement being carried-out before, during or after the tetrapolar impedance measurement.

According to some embodiments of the present disclosure, the embodiment may include a disposable test strip for an electrochemical biosensor equipped with four (4) electrodes within a capillary channel forming a tetrapolar AC impedance sensor, two of these electrodes being current injection electrodes, and the other two, located in-between the current injection electrodes being sense electrodes, with the width of the sense electrodes within the capillary being five hundred (500) micrometers or less.

According to some embodiments of the present disclosure, the embodiment may include a disposable test strip for an electrochemical biosensor equipped with four (4) electrodes within a capillary channel forming a tetrapolar AC impedance sensor, two of these electrodes being current injection electrodes, and the other two, located in-between the current injection electrodes being sense electrodes, and the length of said sense electrodes within the capillary not exceeding half the width of the capillary.

According to some embodiments of the present disclosure, the embodiment may include a disposable test strip for an electrochemical biosensor equipped with four (4) electrodes within a capillary channel forming a tetrapolar AC impedance sensor, two of these electrodes being current injection electrodes, and the other two, located in-between the current injection electrodes being sense electrodes, the length of said sense electrodes within the capillary not exceeding half the width of the capillary and their width within the capillary being five hundred (500) micrometers or less.

According to some embodiments of the present disclosure, the embodiment may include an instrument designed to be coupled to a disposable test strip equipped with a tetrapolar impedance measurement sensor and designed to inject between two electrodes of said strip an AC current programmable in amplitude from 200 nA rms up to 1 mA rms and in frequency from 1 Hz to 10 MHz, with a frequency accuracy of +/−10% or better and an amplitude accuracy of +/−10% or better.

According to some embodiments of the present disclosure, the embodiment may include an instrument designed to be coupled to a disposable test strip equipped with a tetrapolar impedance measurement sensor and designed to inject between two electrodes of said strip an AC current programmable in amplitude and in frequency from 200 nA to 1 mA and 1 Hz to 10 MHz said current being combined with a DC bias current programmable from 0 nA up to 1 mArms, programmable in direction, and the accuracy of currents and frequency being +/−10% or better.

According to some embodiments of the present disclosure, the embodiment may include an instrument designed to be coupled to a disposable test strip equipped with a tetrapolar impedance measurement sensor and designed to inject between two electrodes of said strip an AC current programmable in amplitude and in frequency from 200 nA to 1 mA and 1 Hz to 10 MHz said current being combined with a DC bias current programmable from 0 nA up to 1 mArms, programmable in direction, said currents, frequency and direction being dynamically programmable based on the amplitude and/or phase of the sensed voltage so that an optimum operating range can be established for the instrument.

According to some embodiments of the present disclosure, the embodiment may include an instrument designed to be coupled to a disposable test strip equipped with a tetrapolar impedance measurement sensor and designed to receive and process the signal difference between two tetrapolar sensing electrodes and capable to process input signals having an AC amplitude from 1 uV to 500 mV and a frequency from 1 Hz to 10 MHz, while rejecting signal common to both electrodes.

According to some embodiments of the present disclosure, the embodiment may include an instrument designed to be coupled to a disposable test strip equipped with a tetrapolar impedance measurement sensor and designed to receive and process the signal difference between two tetrapolar sensing electrodes and capable to process signals of a frequency equal to +/−5% or better as the frequency of a current source connected to the other two tetrapolar electrodes (passband function of the sense circuit).

According to some embodiments of the present disclosure, the embodiment may include an instrument designed to be coupled to a disposable test strip equipped with a tetrapolar impedance measurement sensor and designed to receive and process the signal difference between two tetrapolar sensing electrodes and to then measure the phase angle difference between 1) the voltage difference between the two sensing electrodes and 2) a phase reference provided by the circuit injected a programmable AC current between the other two tetrapolar electrodes.

According to some embodiments of the present disclosure, the embodiment may include an instrument designed to be coupled to a disposable test strip equipped with a tetrapolar impedance measurement sensor and one or more analyte sensor(s) and equipped with the necessary switches and signal routing circuits necessary to assign multiple purposes to some of the strip electrodes so that, as determined by the instrument firmware one or more shared electrode(s) can be used for an analyte measurement function, or an impedance measurement function, as determined by the instrument algorithm.

According to some embodiments of the present disclosure, the embodiment may include an instrument designed to be coupled to a disposable test strip equipped with a tetrapolar impedance measurement sensor and one or more analyte sensor(s) and equipped with the necessary switches and signal routing circuits necessary to assign multiple purposes to some of the strip electrodes so that, as determined by the instrument firmware different pairs of electrodes can be used to inject the sample current within the capillary, thus creating different possible ratio between the distance separating the sensing electrodes, and the several possible distances separating the current injection electrodes.

According to some embodiments of the present disclosure, the embodiment may include an instrument designed to be coupled to a disposable test strip equipped with a tetrapolar impedance measurement sensor and one or more analyte sensor(s) and equipped with the necessary switches and signal routing circuits necessary to temporarily connect, internally to the instrument its impedance and phase measurement circuits to precision references used for calibration proposes, as determined by the instrument firmware, for example just before an impedance test, just after or both just before and just after.

Whereas many alterations and modifications of the present disclosure will no doubt become apparent to a person of ordinary skill in the art after having read the foregoing description, it is to be understood that the particular embodiments shown and described by way of illustration are in no way intended to be considered limiting. Further, the disclosure has been described with reference to particular preferred embodiments, but variations within the spirit and scope of the disclosure will occur to those skilled in the art. It is noted that the foregoing examples have been provided merely for the purpose of explanation and are in no way to be construed as limiting of the present disclosure. While the present disclosure has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present disclosure in its aspects. Although the present disclosure has been described herein with reference to particular means, materials and embodiments, the present disclosure is not intended to be limited to the particulars disclosed herein; rather, the present disclosure extends to all functionally equivalent structures, methods and uses, such as are within the scope of the appended claims.

What is claimed is:

1. A test strip comprising:
   a base layer;
   a capillary chamber configured to receive a fluid sample;
   at least two drive electrodes disposed on the base layer to be placed in electrical communication with a current-source ($I_{ac}$) for flowing an AC current provided by the current-source ($I_{ac}$) through the fluid sample in the capillary chamber and between the at least two drive electrodes;
   at least two sense electrodes disposed on the base layer and positioned between the at least two drive electrodes, each of the at least two sense electrodes configured for measuring a difference in an AC potential therebetween to determine an impedance measurement of the fluid sample between the at least two sense electrodes; and
   a conductive trace extending from each of the at least two drive electrodes and running parallel and adjacent to at least one of the at least two sense electrodes to eliminate or reduce the stray capacitances by creating a capacitance bridge between the at least two drive electrodes,
   wherein when the at least two sense electrodes are in direct electrical communication with a high input-impedance voltage measurement circuit to measure the difference in AC potential between the at least two sense electrodes, an impedance measurement is indicative of a hematocrit level in the fluid sample.

2. The test strip of claim 1, wherein the current-source ($I_{ac}$) is programmable in amplitude and frequency.

3. The test strip of claim 1, wherein the current-source ($I_{ac}$) is produced from a power source.

4. The test strip of claim 1, wherein the AC current-source (Iac) is configured to apply the AC current through the fluid sample alternatively from a first one of the at least two drive electrodes to another one of the at least two drive electrodes as determined by a frequency of the AC current provided by the current-source ($I_{ac}$).

5. A test strip comprising:
   a base layer;
   a capillary chamber configured to receive a fluid sample;
   at least two drive electrodes disposed on the base layer to be placed in electrical communication with a current-source ($I_{ac}$) for flowing an AC current provided by the current-source ($I_{ac}$) through the fluid sample in the capillary chamber and between the at least two drive electrodes;
   at least two sense electrodes disposed on the base layer and positioned between the at least two drive electrodes, each of the at least two sense electrodes configured for measuring a difference in an AC potential therebetween to determine an impedance measurement of the fluid sample between the at least two sense electrodes; and
   wherein when the at least two sense electrodes are configured to be connected to a high input-impedance voltage measurement circuit to measure the difference in AC potential between the at least two sense electrodes,
   wherein the voltage measurement circuit includes a voltmeter configured to reduce the AC current flowing between the at least two sense electrodes and the voltmeter when the at least two sense electrodes are in direct electrical communication with the high input-impedance voltage measurement circuit such that the at least two sense electrodes are not subject to an electrode polarization impedance resulting from charge transfer between the at least two sense electrodes and an impedance measurement is indicative of a hematocrit level in the fluid sample.

6. The test strip of claim 5, wherein the at least two sense electrodes of the test strip are in electrical communication with the voltmeter, the voltmeter being capable of measuring the difference in the AC potential between the at least two sense electrodes to determine the impedance measurement, such that the impedance measurement is not subject to an electrode polarization impedance of the at least two drive electrodes.

7. A diagnostic meter comprising:
a channel having a proximal end and a distal end for receiving a test strip;
at least two drive electrode contacts positioned in the channel to contact at least two drive electrodes of the test strip received in the channel;
a current-source ($I_{ac}$) for providing an AC current to the at least two drive electrodes of the test strip via the at least two drive electrode contacts;
at least two sense electrode contacts positioned in the channel to contact at least two sense electrodes of the test strip received in the channel;
a high input-impedance voltage measurement circuit to connect directly to the at least two sense electrodes to measure a difference in AC potential between the at least two sense electrodes wherein an impedance measurement is indicative of a hematocrit level in the fluid sample; and
an instrumentation amplifier for amplifying the measured difference in AC potential between the at least two sense electrodes when in electrical communication with the at least two sense electrode contacts,
wherein an output of the high input-impedance voltage measurement circuit and an output of the current-source ($I_{ac}$) are each coupled to a phase angle detection circuit.

8. The diagnostic meter of claim 7, wherein the proximal end of the channel is flared out to receive the test strip.

9. The diagnostic meter of claim 7, wherein the connector further comprises tangs extending a predetermined height above a base of the channel and wherein the test strip is received between the base of the channel and the tangs.

10. The diagnostic meter of claim 7, further comprising one or more calibration circuits for selective connection between the current-source ($I_{ac}$) and the instrumentation amplifier.

11. The diagnostic meter of claim 7, further comprising one or more of a rectifier, an integrator, an analog to digital converter, a phase-angle detection circuit, or combinations thereof in electrical communication with the instrumentation amplifier.

12. A system for measuring glucose concentration comprising:
a test strip comprising a base layer, a capillary chamber configured to receive a fluid sample, at least two drive electrodes disposed on the base layer for electrical communication with a current-source ($I_{ac}$) for flowing an AC current provided by the current-source ($I_{ac}$) through a fluid sample in the capillary chamber and between the at least two drive electrodes, and at least two sense electrodes disposed on the base layer and positioned between the at least two drive electrodes, the each of the at least two sense electrodes configured for measuring a difference in an AC potential therebetween to determine an impedance measurement of the fluid sample between the at least two sense electrodes wherein the impedance measurement is indicative of a hematocrit level in the fluid sample; and
a diagnostic meter comprising:
a channel having a proximal end and a distal end for receiving the test strip;
at least two drive electrode contacts positioned in the channel to contact the at least two drive electrodes of the test strip received in the channel, the current-source ($I_{ac}$) for providing the AC current to the at least two drive electrodes of the test strip via the at least two drive electrode contacts;
at least two sense electrode contacts positioned in the channel to contact the at least two sense electrodes of the test strip received in the channel;
a high input-impedance voltage measurement circuit that directly connects to the at least two sense electrodes to measure the difference in AC potential between the at least two sense electrodes; and
an instrumentation amplifier for amplifying the measured difference in AC potential between the at least two sense electrodes when in electrical communication with the at least two sense electrode contacts,
wherein an output of the high input-impedance voltage measurement circuit and an output of the current-source ($I_{ac}$) are each coupled to a phase angle detection circuit.

13. The system of claim 12, wherein the current-source ($I_{ac}$) is programmable in amplitude and frequency.

14. The system of claim 12, wherein the current-source ($I_{ac}$) is produced from a power source.

15. The system of claim 12, wherein the AC current flows through the fluid sample alternatively from a first one of the at least two drive electrodes to another one of the at least two drive electrodes as determined by a frequency of the AC current provided by the current-source ($I_{ac}$).

16. The system of claim 12, further comprising one or more of a rectifier, an integrator, an analog to digital converter, a phase-angle detection circuit, or combinations thereof in electrical communication with the instrumentation amplifier.

17. A system for measuring glucose concentration, the system comprising:
a test strip comprising a base layer, a capillary chamber configured to receive a fluid sample, at least two drive electrodes disposed on the base layer for electrical communication with a current-source ($I_{ac}$) for flowing an AC current provided by the current-source ($I_{ac}$) through a fluid sample in the capillary chamber and between the at least two drive electrodes, and at least two sense electrodes disposed on the base layer and positioned between the at least two drive electrodes, the each of the at least two sense electrodes configured for measuring a difference in an AC potential therebetween to determine an impedance measurement of the fluid sample between the at least two sense electrodes wherein the impedance measurement is indicative of a hematocrit level in the fluid sample; and
a diagnostic meter comprising a channel having a proximal end and a distal end for receiving the test strip, at least two drive electrode contacts positioned in the channel to contact the at least two drive electrodes of the test strip received in the channel, the current-source ($I_{ac}$) for providing the AC current to the at least two drive electrodes of the test strip via the at least two drive electrode contacts, at least two sense electrode contacts positioned in the channel to contact the at least two sense electrodes of the test strip received in the channel, and a high input-impedance voltage measurement circuit that directly connects to the at least two sense electrodes to measure the difference in AC potential between the at least two sense electrodes,
wherein the high input-impedance voltage measurement circuit includes a voltmeter configured to reduce the AC current flowing between the at least two sense electrodes, so that the at least two sense electrodes are not subject to an electrode polarization impedance resulting from charge transfer between the at least two sense electrodes.

18. The system of claim 17, wherein when the at least two sense electrodes of the test strip are in electrical communication with the voltmeter, the voltmeter is capable of measuring the difference in the AC potential between the at least two sense electrodes to determine the impedance measurement, such that the impedance measurement is not subject to the electrode polarization impedance of the at least two drive electrodes.

19. The diagnostic meter of claim 17, further comprising one or more calibration circuits for selective connection between the current-source ($I_{ac}$) and an instrumentation amplifier.

20. A method for making a test strip, the method comprising:
providing a base layer;
forming a capillary chamber on the base layer;
forming at least two drive electrodes on the base layer to be placed in electrical communication with a current-source ($I_{ac}$) for flowing an AC current provided by the current-source ($I_{ac}$) through a fluid sample in the capillary chamber and between the at least two drive electrodes; and
forming at least two sense electrodes on the base layer positioned between the at least two drive electrodes such that an AC current flowing through a fluid sample received in the capillary chamber between the at least two drive electrodes flows across each of the at least two sense electrodes for measuring a difference in an AC potential therebetween to determine an impedance measurement of the fluid sample between the at least two sense electrodes,
forming a conductive trace extending from each of the at least two drive electrodes and running parallel and adjacent to at least one of the at least two sense electrodes to eliminate or reduce the stray capacitances by creating a capacitance bridge between the at least two drive electrodes,
wherein when the at least two sense electrodes are in direct electrical communication with a high input-impedance voltage measurement circuit to measure the difference in AC potential between the at least two sense electrodes, an impedance measurement is indicative of a hematocrit level in the fluid sample.

21. The method of claim 20, further comprising forming a fill-detect electrode on the base layer at an end of the capillary chamber for contacting the fluid sample when the capillary chamber is substantially full.

22. A method for measuring glucose concentration, the method comprising:
receiving a fluid sample in a test strip;
flowing, through the fluid sample between two drive electrodes of the test strip, an AC current;
measuring, by a high input-impedance voltage measurement circuit receiving inputs from two sense electrodes positioned between the two drive electrodes, a difference in an AC potential between the two sense electrodes to determine an impedance measurement of the fluid sample between the two sense electrodes; and
outputting, by the high input-impedance voltage measurement circuit, an amplified signal of the difference in an AC potential to a phase angle detection circuit, wherein the impedance measurement is indicative of a hematocrit level in the fluid sample.

23. The method of claim 22, further comprising amplifying, by an instrumentation amplifier in electrical communication with the two sense electrodes, the measured difference in AC potential between the two sense electrodes.

24. The method of claim 22, further comprising providing, by a current-source ($I_{ac}$), the AC current to the first and second drive electrodes.

25. The method of claim 22, further comprising reducing, by the high input-impedance voltage measurement circuit directly connected to the two sense electrodes, the AC current flowing between the two sense electrodes and the high input-impedance voltage measurement circuit such that the two sense electrodes are not subject to an electrode polarization impedance resulting from charge transfer between the two sense electrodes.

26. A test strip comprising:
a base layer;
a capillary chamber configured to receive a fluid sample;
at least two drive electrodes disposed on the base layer to be placed in electrical communication with a current-source ($I_{ac}$) for flowing an AC current provided by the current-source ($I_{ac}$) through the fluid sample in the capillary chamber and between the at least two drive electrodes; and
at least two sense electrodes disposed on the base layer and positioned between the at least two drive electrodes, each of the at least two sense electrodes configured for measuring a difference in an AC potential therebetween to determine an impedance measurement of the fluid sample between the at least two sense electrodes; and
an instrumentation amplifier or buffered differential amplifier as part of a high input-impedance voltage measurement circuit, wherein the instrumentation amplifier or buffered differential amplifier is connected to the at least two sense electrodes to amplify the difference in voltage between the at least two sense electrodes, while rejecting any signal common to both of the at least two sense electrodes,
wherein when the at least two sense electrodes are in direct electrical communication with the high input-impedance voltage measurement circuit to measure the difference in AC potential between the at least two sense electrodes, an impedance measurement is indicative of a hematocrit level in the fluid sample.

27. A system for measuring glucose concentration, the system comprising:
a test strip comprising:
a base layer;
a capillary chamber configured to receive a fluid sample;
at least two drive electrodes disposed on the base layer for electrical communication with a current-source ($I_{ac}$) for flowing an AC current provided by the current-source ($I_{ac}$) through a fluid sample in the capillary chamber and between the at least two drive electrodes;
at least two sense electrodes disposed on the base layer and positioned between the at least two drive electrodes, the each of the at least two sense electrodes configured for measuring a difference in an AC potential therebetween to determine an impedance measurement of the fluid sample between the at least two sense electrodes wherein the impedance measurement is indicative of a hematocrit level in the fluid sample; and
a conductive trace extending from each of the at least two drive electrodes and running parallel and adjacent to at least one of the at least two sense electrodes to eliminate or reduce the stray capacitances by creating a capacitance bridge between the at least two drive electrodes; and a diagnostic meter comprising:
- a channel having a proximal end and a distal end for receiving the test strip;
- at least two drive electrode contacts positioned in the channel to contact the at least two drive electrodes of the test strip received in the channel, the current-source ($I_{ac}$) for providing the AC current to the at least two drive electrodes of the test strip via the at least two drive electrode contacts;
- at least two sense electrode contacts positioned in the channel to contact the at least two sense electrodes of the test strip received in the channel;
- a high input-impedance voltage measurement circuit that directly connects to the at least two sense electrodes to measure the difference in AC potential between the at least two sense electrodes; and
- an instrumentation amplifier as part of the high input-impedance voltage measurement circuit and connected to the at least two sense electrodes to amplify the difference in voltage between the at least two sense electrodes, while rejecting any signal common to both of the at least two sense electrodes.

* * * * *